US009132272B2

(12) United States Patent
Alves et al.

(10) Patent No.: US 9,132,272 B2
(45) Date of Patent: Sep. 15, 2015

(54) METHODS AND SYSTEMS FOR AUTOMATICALLY TURNING ON AND OFF DRG STIMULATION AND ADJUSTING DRG STIMULATION PARAMETERS

(71) Applicant: Spinal Modulation, Inc., Menlo Park, CA (US)

(72) Inventors: Jeffrey M. Alves, Pleasanton, CA (US); April C. Pixley, Los Altos, CA (US); Jeyakumar Subbaroyan, Menlo Park, CA (US); Jeffery M. Kramer, San Francisco, CA (US); Lynn Elliott, Maple Grove, MN (US)

(73) Assignee: SPINAL MODULATION, INC., Menlo Park, CA (US)

( * ) Notice: Subject to any disclaimer, the term of this patent is extended or adjusted under 35 U.S.C. 154(b) by 0 days.

(21) Appl. No.: 14/278,586

(22) Filed: May 15, 2014

(65) Prior Publication Data
US 2014/0343623 A1   Nov. 20, 2014

Related U.S. Application Data

(60) Provisional application No. 61/824,170, filed on May 16, 2013.

(51) Int. Cl.
*A61N 1/36* (2006.01)

(52) U.S. Cl.
CPC ........ *A61N 1/36057* (2013.01); *A61N 1/36071* (2013.01); *A61N 1/36139* (2013.01); *A61N 1/36153* (2013.01); *A61N 1/36157* (2013.01);
(Continued)

(58) Field of Classification Search
None
See application file for complete search history.

(56) References Cited

U.S. PATENT DOCUMENTS 6,871,099 B1   3/2005   Whitehurst et al.
7,450,993 B2   11/2008  Kim et al.
7,894,905 B2   2/2011   Pless et al.
(Continued)

FOREIGN PATENT DOCUMENTS

WO   2010045481 A2   4/2010
WO   2012075337 A2   6/2012

OTHER PUBLICATIONS

International Search Report and Written Opinion dated Aug. 27, 2014, in International Patent Appl. No. PCT/US2014/038348 filed May 16, 2014.
(Continued)

*Primary Examiner* — Brian T Gedeon
*Assistant Examiner* — Ankit Tejani
(74) *Attorney, Agent, or Firm* — Vierra Magen Marcus LLP

(57) ABSTRACT

Methods and systems described herein can be used to automatically turn on and off stimulation of a target dorsal root ganglion (DRG) and/or adjust stimulation parameters. At least one of an input signal (indicative of an electrical field resulting from an electrical signal propagated by adjacent distal sensory nerve fibers toward the target DRG), an output signal (indicative of an electrical field resulting from an electrical signal propagated by adjacent proximal sensory nerve fibers away from the target DRG) or a DRG signal (indicative of an electrical field produced by cell bodies of primary sensory neurons within the target DRG and resulting from an electrical signal propagated by sensory nerve fibers within the target DRG) is/are obtained and analyzed. Delivery of electrical stimulation is turned on and off and/or at least one of pulse amplitude, pulse width and/or pulse repetition rate is/are adjusted based on results of the analysis.

35 Claims, 6 Drawing Sheets

(52) U.S. Cl.
CPC ......... *A61N 1/36171* (2013.01); *A61N 1/36175* (2013.01)

(56) References Cited

U.S. PATENT DOCUMENTS

| | | |
|---|---|---|
| 2010/0137938 A1 | 6/2010 | Kishawi et al. |
| 2010/0305675 A1* | 12/2010 | Laske et al. ................... 607/122 |
| 2011/0054565 A1 | 3/2011 | Wacnik et al. |
| 2011/0118661 A1 | 5/2011 | Pless et al. |
| 2012/0277839 A1 | 11/2012 | Kramer et al. |
| 2013/0197338 A1 | 8/2013 | Yu et al. |

OTHER PUBLICATIONS

Deer et al, "A Prospective Study of Dorsal Root Ganglion Stimulation for the Relief of Chronic Pain", Neromodulation: Technology at the Neural Interface, Jan. 2013, pp. 67-72.

* cited by examiner

METHODS AND SYSTEMS FOR AUTOMATICALLY TURNING ON AND OFF DRG STIMULATION AND ADJUSTING DRG STIMULATION PARAMETERS

PRIORITY CLAIM

This application claims priority to U.S. Provisional Patent Application No. 61/824,170, filed May 16, 2013, which is incorporated herein by reference.

FIELD OF THE INVENTION

Embodiments of the present invention generally relate to methods and systems for automatically turning on and off stimulation of a target dorsal root ganglion (DRG), and for automatically adjusting stimulation parameters used when stimulating the target DRG.

BACKGROUND OF THE INVENTION

It has recently been discovered that directly neuromodulating one or more target dorsal root ganglion (DRG) can be used to treat various types of conditions associated with or influenced by the nervous system. Such neuromodulating often involves stimulating one or more target DRG for the purpose of treating pain. However, other types of conditions that can be treated by stimulating target DRG include itching, Parkinson's Disease, Multiple Sclerosis, movement disorders, spinal cord injury, asthma, chronic heart failure, obesity and stroke (particularly acute ischemia), to name a few.

Neuromodulation of a target DRG can be achieved using an implantable neurostimulator (INS) that is implanted within a patient. More specifically, one or more leads, each including one or more electrodes, is/are also implanted within the patient and connected to the INS to enable the INS to deliver electrical stimulation therapy to a target DRG using electrodes of the lead(s). The INS is typically in wireless communication with an external patient programmer that enables the patient to manually turn on and off the delivery of stimulation, as well as to enable the patient to adjust stimulation parameters, such as stimulation pulse amplitude and/or stimulation pulse repetition rate, depending on how the patient is currently feeling.

Accordingly, the patient typically needs to carry around the patient programmer to enable them to adjust their stimulation. This is due to the fact that a patient's desire for therapy, and a patient's desired level of therapy, may vary over time. If the INS is delivering electrical stimulation therapy to a target DRG during periods of time when the patient is not in need of such therapy, energy is wasted. Further, if stimulation parameters are set higher than necessary to treat the targeted pain, energy is also wasted. Wasting energy may result in needing to frequently replace the INS, which involves surgically explanting an INS and implanting a replacement INS. If the INS is not delivering electrical stimulation therapy to a target DRG during periods of time when the patient is need of such therapy, the patient may be uncomfortable. Further, if stimulation parameters are set too low, the patient will not receive the desired pain relief, and thus, the patient may be uncomfortable.

BRIEF SUMMARY

Certain embodiments of the present invention are related to implantable systems that include an implantable neurostimulator (INS) to which is connected one or more leads each having one or more electrodes, as well as to methods for use with such systems. Some such methods are for efficiently treating targeted pain in a patient by selectively delivering electrical stimulation to a target dorsal root ganglion (DRG). The target DRG is connected between adjacent distal sensory nerve fibers and adjacent proximal sensory nerve fibers, wherein the adjacent distal sensory nerve fibers propagate an electrical signal from a periphery of the patient toward the target DRG, and the adjacent proximal sensory nerve fibers propagate an electrical signal away from the target DRG toward a central nervous system of the patient.

In accordance with certain embodiments, the INS includes a pulse generator, sensing circuitry and a controller. The pulse generator, under control of the controller, generates electrical stimulation pulses that can be delivered to a target DRG via one or more electrodes of one or more leads. The sensing circuitry, under control of the controller, uses at least one of the one or more electrodes of the one or more leads to obtain at least one of an input signal (indicative of an electrical field resulting from an electrical signal propagated by the adjacent distal sensory nerve fibers toward the target DRG), an output signal (indicative of an electrical field resulting from an electrical signal propagated by the adjacent proximal sensory nerve fibers away from the target DRG) or a DRG signal (indicative of an electrical field produced by cell bodies of primary sensory neurons within the target DRG and resulting from an electrical signal propagated by sensory nerve fibers within the target DRG).

In accordance with certain embodiments, one or more of the aforementioned obtained signals is/are analyzed (e.g., by the controller), and the delivering of electrical stimulation is selectively turned on and off based on results of the analysis. Additionally, or alternatively, one or more of the obtained signals is/are analyzed (e.g., by the controller), and at least one of pulse amplitude, pulse width or pulse repetition rate of electrical pulses that are used for delivering electrical stimulation to the target DRG is/are adjusted based on results of the analysis.

In certain embodiments, both the input signal (indicative of an electrical field resulting from an electrical signal propagated by the adjacent distal sensory nerve fibers toward the target DRG) and the output signal (indicative of an electrical field resulting from an electrical signal propagated by the adjacent proximal sensory nerve fibers away from the target DRG) are obtained. This enables the output signal to be compared to the input signal, and the delivery of the electrical stimulation to the target DRG to be selectively turned on and off based on results of the comparison. Additionally, or alternatively, at least one of pulse amplitude, pulse width or pulse repetition rate of electrical pulses that are used for delivering electrical stimulation to the target DRG is/are adjusted based on results of the comparison.

In certain embodiments, there is a determination of an input metric and an output metric, and the output metric is compared to the input metric. In certain embodiments, the input metric is indicative of how many pulses occur during a specified time period of the input signal, and the output metric is indicative of how many pulses occur during a specified time period of the output signal. In certain embodiments, the input metric is indicative of an amplitude of pulses of the input signal, and the output metric is indicative of an amplitude of pulses of the output signal. In some embodiments, the input metric is indicative of a width of pulses of the input signal, and the output metric is indicative of a width of pulses of the output signal.

In certain embodiments, the DRG signal (indicative of an electrical field produced by cell bodies of primary sensory neurons within the target DRG and resulting from an electrical signal propagated by sensory nerve fibers within the target DRG) is obtained and a DRG metric of the DRG signal is determined and compared to a corresponding threshold. In some such embodiments delivery of electrical stimulation to the target DRG is selectively turned on and off based on results of this comparison. Additionally, or alternatively, at least one of pulse amplitude, pulse width or pulse repetition rate of electrical pulses that are used for delivering electrical stimulation to the target DRG is/are adjusted based on results of this comparison. In certain embodiments, the DRG metric is indicative of how many pulses occur during a specified time period of the DRG signal. In certain embodiments, the DRG metric is indicative of an amplitude of pulses of the DRG signal. In certain embodiments, the DRG metric is indicative of a width of pulses of the DRG signal.

In certain embodiments, morphology of the DRG signal is compared to one or more stored morphological templates, and the delivery of the electrical stimulation to the target DRG is selectively turned on and off based on results of this comparison. Additionally, or alternatively, at least one of pulse amplitude, pulse width or pulse repetition rate of electrical pulses that are used for delivering electrical stimulation to the target DRG is/are adjusted based on results of this comparison.

In certain embodiments, frequency content of the DRG signal is compared to stored information indicative of frequency content, and delivery of the electrical stimulation to the target DRG is selectively turned on and off based on results of this comparison. Additionally, or alternatively, at least one of pulse amplitude, pulse width or pulse repetition rate of electrical pulses that are used for delivering electrical stimulation to the target DRG is/are adjusted based on results of this comparison.

In certain embodiments, the output signal (indicative of an electrical field resulting from an electrical signal propagated by the adjacent proximal sensory nerve fibers away from the target DRG) is obtained and an output metric of the output signal is determined and compared a corresponding threshold. In some such embodiments delivery of electrical stimulation to the target DRG is selectively turned on and off based on results of this comparison. Additionally, or alternatively, at least one of pulse amplitude, pulse width or pulse repetition rate of electrical pulses that are used for delivering electrical stimulation to the target DRG is/are adjusted based on results of this comparison. In certain embodiments, the output metric is indicative of how many pulses occur during a specified time period of the output signal. In certain embodiments, the output metric is indicative of an amplitude of pulses of the output signal. In certain embodiments, the output metric is indicative of a width of pulses of the output signal.

In certain embodiments, morphology of the output signal is compared to one or more stored morphological templates, and the delivery of the electrical stimulation to the target DRG is selectively turned on and off based on results of this comparison. Additionally, or alternatively, at least one of pulse amplitude, pulse width or pulse repetition rate of electrical pulses that are used for delivering electrical stimulation to the target DRG is/are adjusted based on results of this comparison.

In certain embodiments, frequency content of the output signal is compared to stored information indicative of frequency content, and delivery of the electrical stimulation to the target DRG is selectively turned on and off based on results of this comparison. Additionally, or alternatively, at least one of pulse amplitude, pulse width or pulse repetition rate of electrical pulses that are used for delivering electrical stimulation to the target DRG is/are adjusted based on results of this comparison.

This summary is not intended to summarize all of the embodiments of the present invention. Further and alternative embodiments, and the features, aspects, and advantages of the embodiments of invention will become more apparent from the detailed description set forth below, the drawings and the claims.

DETAILED DESCRIPTION

Figure 1A:
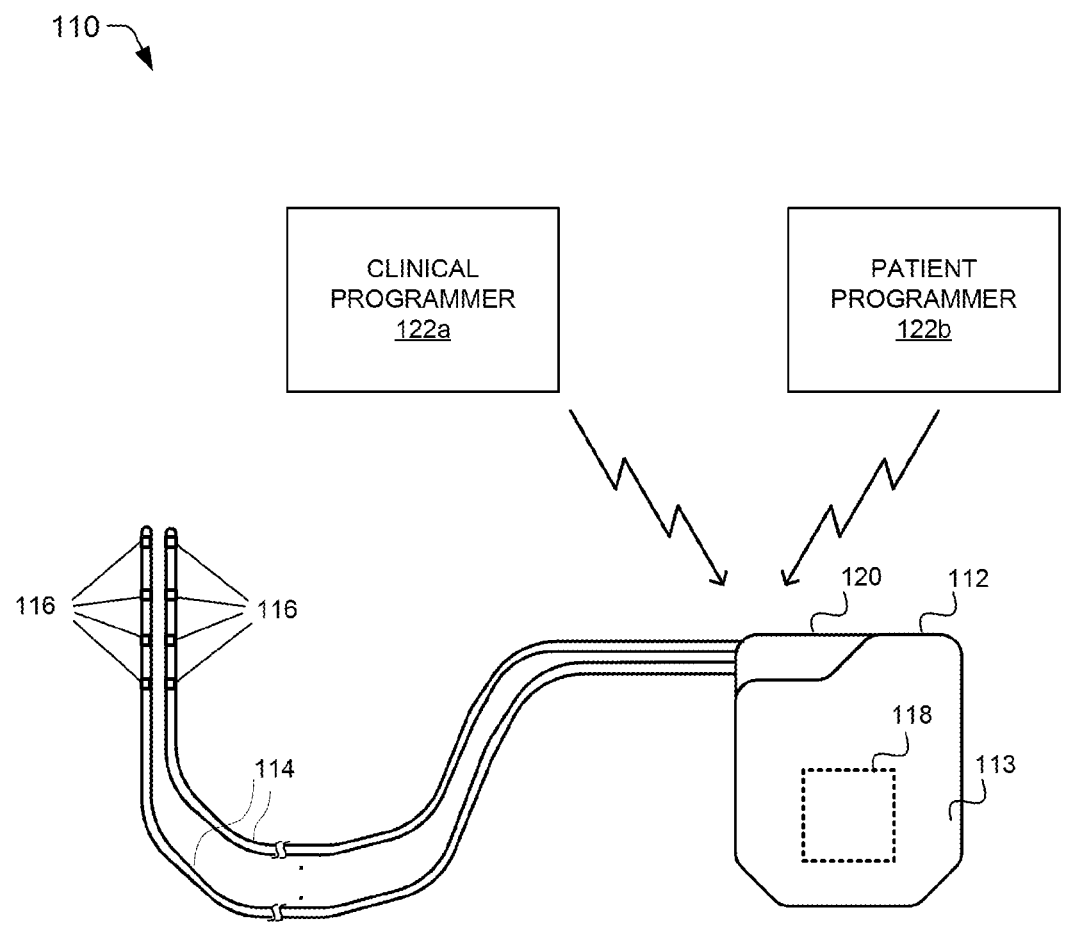
FIG. 1A illustrates an exemplary neurostimulation system with which embodiments of the present invention can be implemented.

The following description is of various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

As mentioned above, a patient within which an INS is implanted typically needs to carry around the patient programmer to enable the patient to adjust their stimulation. This is due to the fact that a patient's desire for therapy, and a patient's desired level of therapy, may vary over time. As also mentioned above, if the INS is delivering electrical stimulation therapy to a target DRG during periods of time when the patient is not in need of such therapy, energy is wasted. Further, if stimulation parameters are set higher than necessary to treat the targeted pain, energy is also wasted. Wasting energy may result in needing to frequently replace the INS, which involves surgically explanting an INS and implanting a replacement INS. Conversely, if the INS is not delivering electrical stimulation therapy to a target DRG during periods of time when the patient is need of such therapy, the patient may be uncomfortable. Further, if stimulation parameters are set too low, the patient will not receive the desired pain relief, and thus, the patient may be uncomfortable.

It is further noted that delivering excess energy to a DRG can overstimulate primary cell bodies of the DRG and potentially compromise the effectiveness of the pain relief therapy. Ideally, DRG stimulation should be such that it exceeds a DRG activation threshold but is below a sensory threshold, wherein the sensory threshold is the threshold at which a patient experiences paresthesia, and wherein the activation threshold is the threshold at which an action potential is elicited in a nerve cell or cell function is modulated. However, there are some patients that prefer to experience paresthesia. Since the cell bodies in neuropathic pain conditions are in a state of hyperexcitability, a relatively low amount of energy is required to activate them. Hence, controlling DRG stimulation is important for achieving optimal or near optimal therapeutic response.

Certain embodiments of the present invention, which are described herein, are related to methods, devices and systems that can be used to selectively turning on and off delivery of the electrical stimulation to a target DRG without any action on the part of the patient. Beneficially, such embodiments can save energy, and thereby extend the useful life of an INS. Additionally, such embodiments can improve a patient's comfort level by automatically turning on stimulation to a target DRG when a patient is experiencing pain that can be relieved using such stimulation.

Certain embodiments of the present invention, which are described herein, are related to methods, devices and systems that can be used to adjust electrical stimulation parameters used to stimulate a target DRG without any action on the part of the patient. Beneficially such embodiments can improve a patient's comfort level. Such embodiments can also save energy, and thereby extend the useful life of an INS.

Prior to providing additional details of such embodiments, an exemplary system in which embodiments of the present invention can be implemented will first be described.

Exemplary Neurostimulation System

An example neurostimulation system 110 is illustrated in FIG. 1A. In this embodiment, the system 110 includes an INS 112, which is typically implantable in a subcutaneous pocket within a patient's body. One or more leads 114 are connected to the INS 112, with each lead including one or more electrodes 116. For example, four leads 114 can be connected to the INS 112, with each lead including four electrodes 116. Alternatively, more or less leads can be used, with more or less electrodes per lead. The INS 112 includes electronic circuitry 118 contained within a housing 113 (also referred to as the "case" or "can") of the INS. The electrodes 116 are electrically coupled to the electronic circuitry 118 by coupling the leads 114 to a connector 120 (also known as a header) of the INS 112.

During an implant procedure, the electrodes 116 can be placed, e.g., within, touching or near the target nerve tissue, such as a target DRG, but is not limited thereto. When a given electrode is selected to receive an electrical stimulus, it is (for purposes of the present invention) said to be "activated" or used to deliver neurostimulation. When an electrode is not selected to receive an electrical stimulus, it is said to be "non-activated," "inactive," "neutral," or not used to deliver neurostimulation. Electrical neurostimulation (also referred to as electrical stimulation, or simply stimulation) occurs between two or more electrodes so that the electrical current associated with the stimulus has a path from the INS 112 to the tissue to be stimulated, and a return path from the tissue to the INS 112. Bipolar stimulation occurs when two of the electrodes of the leads 116 are activated, e.g., when one electrode 116 is activated as an anode at the same time that another electrode 116 is activated as a cathode. Tripolar stimulation occurs when three of the electrodes 116 of the lead(s) 114 are activated, e.g., two electrodes 116 can be activated as an anode at the same time that another electrode 116 is activated as a cathode. In general, multipolar stimulation occurs when multiple electrodes 116 of the lead(s) 114 are activated.

The electronic circuitry 118 can be used to generate and provide an electrically stimulating signal (also referred to as a neurostimulation signal, a neurostimulation waveform, or simply a stimulation signal) to a nerve tissue via at least two of the electrodes 116, with at least one of the electrodes connected as an anode, and at least one of the electrodes connected as a cathode. As described in more detail below, the electronic circuitry can comprise and/or be included within a controller (e.g., processor) for controlling the operations of the device, including stimulating, signal transmission, charging and/or using energy from a battery for powering the various components of the circuitry, and the like.

A programmer can be used to control the INS 112 and/or to program various neurostimulation parameters and/or other instructions into the electronic circuitry 118 of the INS 112. There are generally two types of programmers, both of which can be handheld and capable of wireless communication with the INS 112. The programmer represented by block 122a, which is often referred to as a "clinical programmer" (or sometimes referred to as a "clinician programmer"), may be used by a representative of the INS manufacturer, a clinician, a physician and/or other medical personnel (any of which can be referred to hereafter as a "programming person" or as a "user"). Block 122b represents another type of programmer, which is often referred to as a "patient programmer," which is primarily intended to be controlled by the patient being treated by the INS 112. The programmers 122a and 122b can be referred to hereafter collectively or individually as a programmer 122.

The programmer 122 can include a processor (or other type of controller) and memory that can store one or more code modules. The processor or other controller can execute one or more code modules to perform programming of the INS 112 based on a programming protocol, input from a programming person and feedback from a patient. For example, the programmer 122 can transmit instructions to the INS 112 that instruct the INS to turn on or off stimulation, adjust certain parameters, test specific neurostimulation parameters and/or program certain parameters as those to be used by the INS for chronic treatment of pain.

The programmer 122a or 122b may include (or be coupled to) telemetry circuitry that communicates with the electronic circuitry 118 via radio frequency (RF) or other wireless signals. Regardless whether the telemetry circuitry is within a programmer or coupled to the programmer, the programmer can be said to include telemetry circuitry. The INS 112 can similarly include a processor (or other type of controller) that can execute code modules stored in memory of the INS.

Additional details regarding such neurostimulation are provided in U.S. Pat. No. 7,450,993, entitled "Methods for Selective Stimulation of a Ganglion", and U.S. patent application Ser. No. 12/607,009, entitled "Selective Stimulation Systems and Signal Parameters for Medical Conditions", both of which are incorporated herein by reference.

Exemplary INS

Figure 1B:
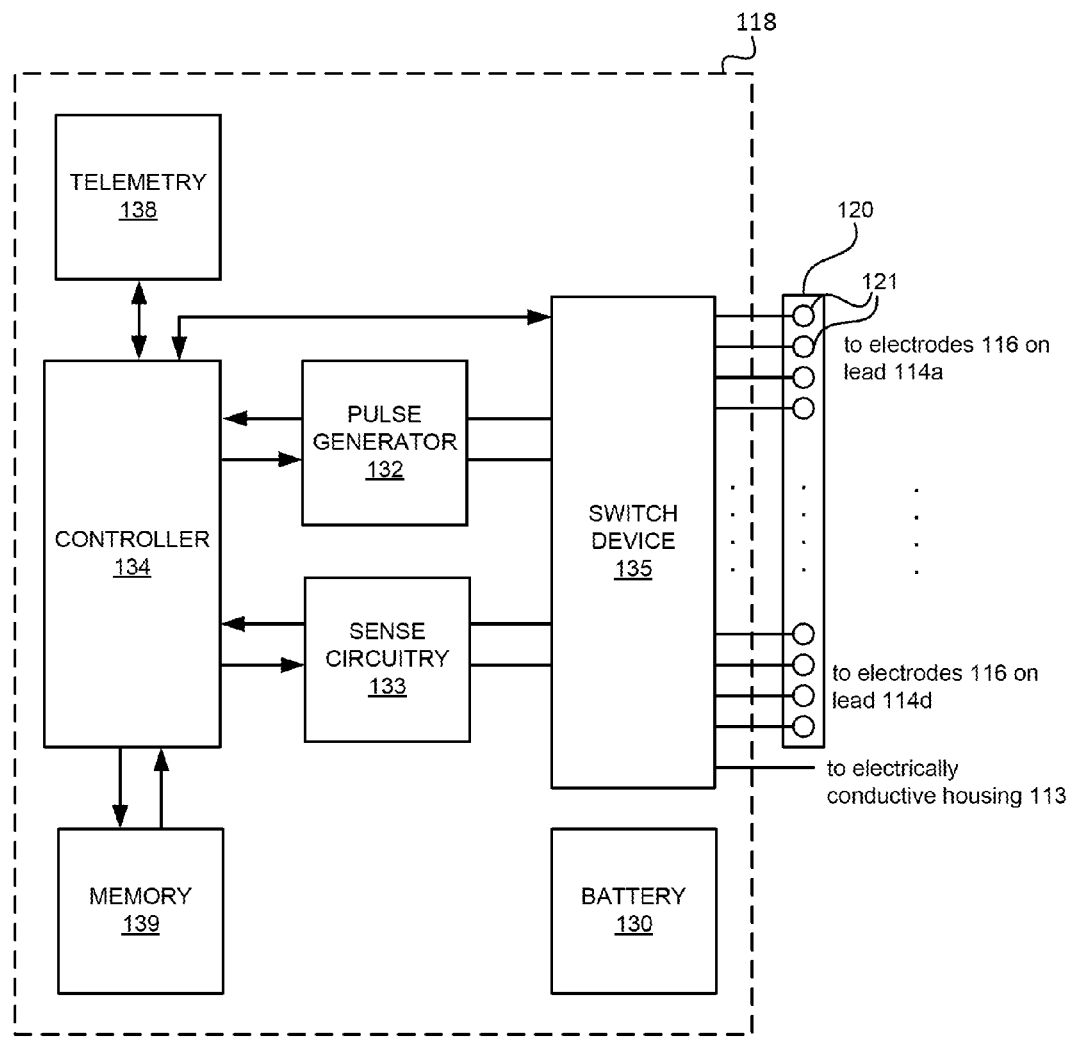
FIG. 1B is a simplified block diagram that illustrates possible components of the electronic circuitry of the INS shown in FIG. 1A.

FIG. 1B is a simplified block diagram that illustrates possible components of the electronic circuitry 118 of the INS 112 shown in FIG. 1A. Referring to FIG. 1B, the electronic circuitry 118 is shown as including a battery 130, a pulse generator 132, sense circuitry 133, a controller 134, a switch device 135, telemetry circuitry 138 and memory 139.

The battery 130 can be used to power the various other components of the electronic circuitry 118. Further, the battery 130 can be used to generate stimulation pulses. As such, the battery 130 can be coupled to the pulse generator 132, the sense circuitry 133, the controller 134, the switch device 135, the telemetry circuitry 138 and the memory 139. One or more voltage regulators (not shown) can step up or step down a voltage provide by the battery 130 to produce one or more predetermined voltages useful for powering such components of the electronic circuitry 118.

The pulse generator 132 can be selectively coupled to electrodes 116 of one or more of the lead(s) 114 via the switch device 135. The pulse generator 132 can include circuitry, including components such as capacitors, resistors, transistors, and/or the like, which are used to generate stimulation pulses, as is well known in the art. The pulse generator 132 can be a single- or multi-channel pulse generator, and can be capable of delivering a single stimulation pulse or multiple stimulation pulses at a given time via a single electrode combination or multiple stimulation pulses at a given time via multiple electrode combinations. More generally, the pulse generator 132 generates electrical stimulation pulses that can be delivered to a target DRG via one or more electrodes 116 of one or more leads 114.

The sense circuitry 133 can be selectively coupled to one or more of the electrodes 116 of the lead(s) 114 and/or to the electrically conductive housing 113 (also known as the "can") via the switch device 135. The sense circuitry 133 can include one or more filters, multiplexers, amplifiers and/or analog-to-digital (A/D) converters, as well as other electronic components, as is known in the art. The filter(s) can be used to filter out frequencies that are not of interest from the sensed signals. Such filter(s) can also be used to determine the frequency content of sensed signals. An exemplary frequency range of interest for complex action potentials can be from about 100 Hz to 10 KHz, however embodiments described herein should not be limited to just this range. The multiplexer(s) can be used to enable sensed signals of different frequency ranges to be analyzed in a time multiplexed manner. The multiplexer(s) can also be used to enable multiple sensed signals indicative of the potential differences between multiple different sensing vectors to be obtained in a time multiplexed manner. The amplifier(s), which can include programmable gain and/or automatic gain control, can be used to increase the amplitude of the sensed signals. The A/D converter(s) can be used to convert sensed analog signals to digital signals that can be analyzed or otherwise operated on by the controller 134. The sense circuitry 133 can be coupled to specific electrodes 116 of a lead 114 or to the "can" 113 via the switch device 135. In accordance with certain embodiments described herein, the sense circuitry 133 is used to sense one or more of an input signal (indicative of an electrical field resulting from an electrical signal propagated by the adjacent distal sensory nerve fibers toward the target DRG), an output signal (indicative of an electrical field resulting from an electrical signal propagated by the adjacent proximal sensory nerve fibers away from the target DRG) or a DRG signal (indicative of an electrical field produced by cell bodies of primary sensory neurons within the target DRG and resulting from an electrical signal propagated by sensory nerve fibers within the target DRG). As will be discussed in additional detail below, the sensing circuitry 133, or portions thereof (e.g., one or more amplifiers of the sensing circuitry) can be disconnected from sensing vector electrodes during the delivery of stimulation, to prevent saturation of the sensing circuitry or portions thereof (e.g., to prevent amplifier saturation). Such circuitry, or portions thereof, may be purposely biased during periods of disconnection, do that once such circuitry is reconnected to sensing vector electrodes, sensed signals can be substantially immediately obtained.

The controller 134 can control the pulse generator 132 to generate stimulation pulses, and control the switch device 135 to couple the stimulation energy to selected electrodes 116 of one or more selected leads 114. Additionally, the controller 134 can control the switch device 135 to select different electrode configurations for delivery of stimulation energy from the pulse generator 132. More specifically, the controller 134 can control the pulse generator 132 and the switch device 135 to deliver stimulation energy in accordance with selected neurostimulation parameters. Such neurostimulation parameters can specify a lead, an electrode configuration for the specified lead, and one or more pulse parameters. For example, where there are four leads, a set of neurostimulation parameters can specify which of the four leads is selected. Where each lead includes four electrodes, a set of neurostimulation parameters can specify how each of the four electrodes of a selected lead is configured, e.g., as an anode (having a positive polarity), a cathode (having a negative polarity), or as an inactive electrode (in which case the electrode is not used for delivering stimulation energy). Exemplary programmable pulse parameters that can be specified include pulse amplitude, pulse width, and pulse frequency (also known as pulse repetition rate) for a stimulation signal. Additionally, the controller 134 can control the switch device 135 to select different sensing vectors used for obtaining signals that are analyzed in accordance with various embodiments of the present invention. The controller 144 can perform the analysis of such sensed signals. Further, the controller 114 can control the selective turning on and off of stimulation and/or the adjusting of stimulation parameters based on results of signal analysis. The controller 134 can include one or more of a microprocessor, a microcontroller, a digital signal processor (DSP), an application specific integrated circuit (ASIC), a field-programmable gate array (FPGA), a state machine, or similar discrete and/or integrated logic circuitry.

The switch device 135 can include a switch array, switch matrix, multiplexer, and/or any other type of switching device suitable to selectively couple connector terminals 121 of the connector 120 to the pulse generator 132 and/or the sense circuitry 133. The connector 120, which includes the connector terminals 121, is used to connect the INS 112 to a proximal end of each lead(s) 114. In this manner, individual electrodes 114 of the lead(s) 116 can be selectively coupled to the pulse generator 132 and/or the sense circuitry 133. Additionally, the switch device 135 can be used to selectively couple the electrically conductive housing 113 (also referred to as the "can") to the sense circuitry 133.

The telemetry circuitry 138 allows the controller 134 to communicate with a programmer 122, and potentially with other devices. The telemetry circuitry 138 can include an RF transceiver that is connected to an antenna (not shown).

Various neurostimulation parameters can be stored in the memory 139, examples of which are discussed herein. The memory can also store thresholds, morphological templates and/or frequency content information that is/are used for analyzing sensed signals in accordance with various embodiments of the present invention. The memory 139 can include RAM, ROM, NVRAM, EEPROM or flash memory, but is not limited thereto.

Exemplary Programmer

Figure 1C:
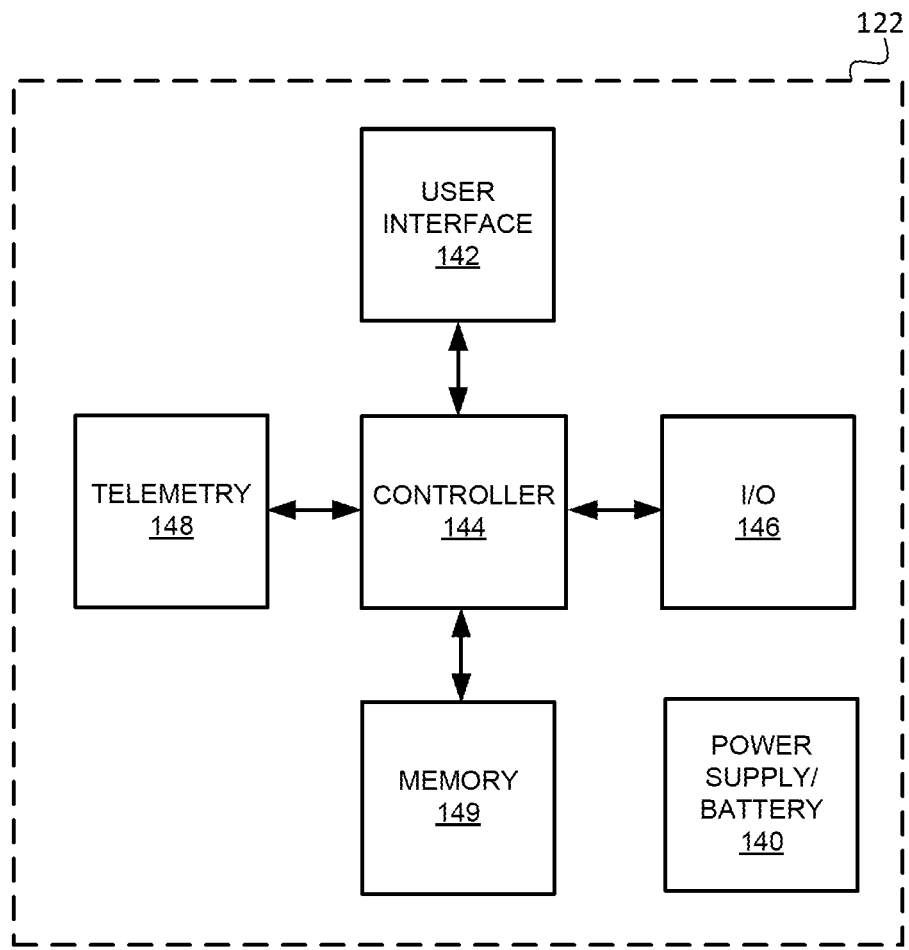
FIG. 1C is a simplified block diagram that illustrates possible components of the clinical programmer or patient programmer shown in FIG. 1A.

FIG. 1C is a simplified block diagram that illustrates possible components of the clinical programmer 122a or patient programmer 122b shown in FIG. 1A, which collectively or individually can be referred to simply as a programmer 122. Referring to FIG. 1C, the programmer 122 is shown as including a power supply 140, a user interface 142, a controller 144, input and output (I/O) circuitry 146, telemetry circuitry 148 and memory 149.

The power supply 140, which can include a battery, can be used to power the various other components of the programmer 122. As such, the power supply 140 can be coupled to the user interface 142, the controller 144, the I/O circuitry 146, the telemetry circuitry 148 and the memory 149. One or more voltage regulators (not shown) can step up or step down a voltage provided by a battery or an external power source to produce one or more predetermined voltages useful for powering such components of the programmer 122.

Where the programmer 122 is a clinical programmer 122a, a programming person may interact with the controller 144 via the user interface 142 in order to test various sets of neurostimulation parameters, input user feedback, select preferred or optimal neurostimulation parameters, and the like. Where the programmer 122 is a patient programmer 122b, a patient can interact with the controller 144 via the user interface 142 in order to turn on and off, select, modify or otherwise control delivery of neurostimulation therapy. For example, the patient may be able to select among various sets of neurostimulation parameters that are stored in the memory 149. Additionally, or alternatively, the patient may be able to increase or decrease specific neurostimulation signal parameters, such as pulse amplitude, to tailor the therapy to the pain being experienced at the time. The user interface 142 can additionally, or alternatively, provide various other functions.

The user interface 142 can include a display, a keypad, a touch screen, mechanical buttons, one or more peripheral pointing devices (e.g., a mouse, touchpad, joystick, trackball, etc.), and/or the like. The controller 144 can provide a graphical user interface (GUI) via the user interface 142 to facilitate interaction with a patient, clinician or physician. Alternative types of user interfaces, e.g., such as one that relies primarily on mechanical type buttons, knobs, switches, etc. may also be used. It is also possible that the programmer 122 include voice recognition capabilities, so that feedback received from the patient and/or programming person can be accepted verbally by the programmer 122. The user interface 142 of the patient programmer 122b often, but not necessarily, provides less capabilities than the user interface 142 of the clinical programmer 122a. The controller 144 and the I/O circuitry 146 of the patient programmer can be similar to, but will likely include less capabilities than, the controller 144 and the I/O circuitry 146 of the clinical programmer 122a.

The controller 144 can send instructions to the INS 112 via the telemetry circuit 148 to cause the testing of various sets of neurostimulation parameters, the sensing of various signals, as well as the saving of various thresholds and templates, but is not limited thereto. For example, the controller 144 can effectuate the sensing, by the INS 112, of various signals that can be used by the INS 112 to selectively turn on and off stimulation and/or adjust stimulation parameters. The controller 144 can include one or more of a microprocessor, a microcontroller, a digital signal processor (DSP), an application specific integrated circuit (ASIC), a field-programmable gate array (FPGA), a state machine, or similar discrete and/or integrated logic circuitry, but is not limited thereto.

The I/O circuitry 146 can include one or more transceivers for wireless communication, ports for wired communication and/or communication via removable electrical media, and/or appropriate drives for communication via removable magnetic or optical media. The I/O circuitry 146 allows the controller 144 to communicate with another device, such as another programmer. The controller 144 can receive selections of, or adjustments to, sets of neurostimulation parameters made by a user (e.g., a physician or patient) via the user interface 142, and can transmit the selection or adjustment to the INS 112 via telemetry circuitry 148. Where the programmer 122 stores data relating to sets of neurostimulation parameters in the memory 149, the controller 144 can receive such data from the programmer 122 via the I/O circuitry 146 during programming by a clinician or physician. In certain embodiments, a patient programmer 122b can use the telemetry circuitry 148 to upload, from the INS 112, sets of neurostimulation parameters that have been programmed into the INS 112 by a clinical programmer 122a.

The telemetry circuitry 148 allows the controller 144 to communicate with INS 112, and potentially with other devices. The telemetry circuitry 148 can include an RF transceiver that is connected to an antenna (not shown).

The memory 149 can include program instructions that, when executed by the controller 144, cause the programmer 122a to perform at least some of the functions described herein. For example, the controller 144 can execute program instructions that specify protocols for testing various sets of neurostimulation parameters and selecting one or more preferred sets of neurostimulation parameters. The memory 149 can also store one or more sets of neurostimulation parameters determined to treat targeted pain for a patient, along with information about the patient. In some embodiments, the memory 149 can store data related to sets of neurostimulation parameters that are available to be selected by the patient for delivery of neurostimulation therapy to the patient being treated by the INS 112. In some embodiments, the controller 144 can record usage information and store usage information in the memory 149. The memory 149 can include program instructions that, when executed by the controller 144, cause the programmer 122 to perform functions ascribed to the programmer 122. The memory 149 can include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Exemplary Neurostimulation Signal

Figure 1D:
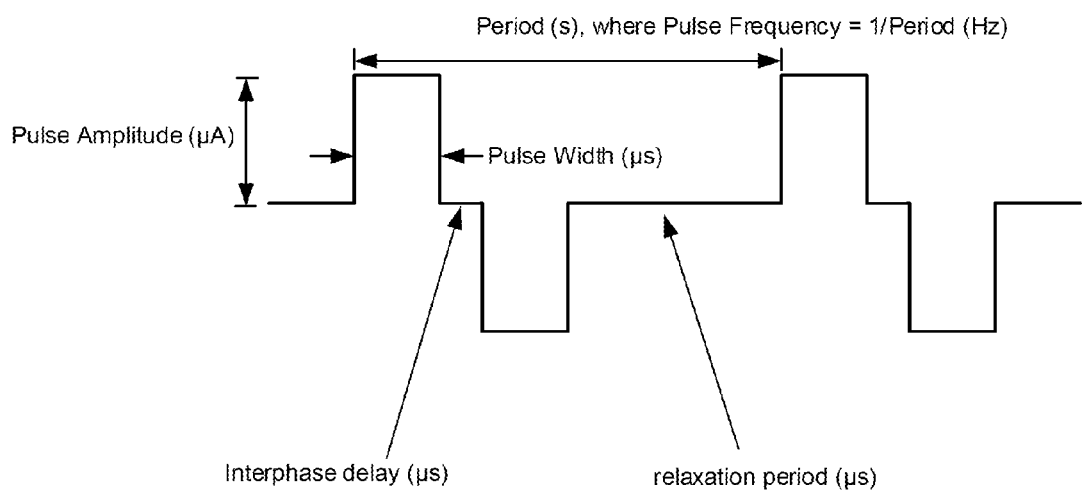
FIG. 1D is used to illustrate exemplary pulse parameters of an exemplary neurostimulation signal that includes biphasic pulses.

FIG. 1D is used to illustrate exemplary pulse parameters of an exemplary neurostimulation signal that includes biphasic pulses. The pulse parameters include pulse amplitude, pulse width and pulse frequency. In FIG. 1D the pulse amplitude is shown as specifying a baseline-to-peak amplitude, but can alternatively define a peak-to-peak amplitude. The pulse amplitude can be specified, e.g., in microamps (μA) and/or millivolts (mV), but is not limited thereto. The pulse width can be specified, e.g., in microseconds (μs), but is not limited thereto. The pulse frequency (also known as pulse repetition rate) can be specified, e.g., in hertz (Hz), but is not limited thereto.

Each biphasic pulse is shown as including a positive portion and a negative portion. In one embodiment, the negative portion of the biphasic stimulation pulse can be achieved by inverting the anode/cathode configuration that was used to achieve the positive portion of the biphasic pulse, but this need not be the case. In FIG. 1D, the positive and negative portions of the biphasic pulse are separated by an interphase delay, which can be fixed or can be programmable. It is also possible that there is no interphase delay. Consecutive pulses can be separated by a baseline relaxation period, during which residual charge on electrodes used to deliver the stimulation pulse may be discharged. FIG. 1D has been included solely to explain an exemplary neurostimulation signal having corresponding exemplary pulse parameters. However, embodiments of the present invention can be used to provide various other types of neurostimulation signals. For example, neurostimulation signals that includes pulses other than biphasic pulses can be used, e.g., monophasic or triphasic pulses can be used, or other types of biphasic pulses can be used. These are just examples, which are not meant to be limiting.

Exemplary Lead Placement

The neurostimulation system 110 can be used to stimulate a variety of anatomical locations within a patient's body and sense signals at a variety of anatomical locations within the patient's body. In some embodiments, the system 110 is used to stimulate one or more target dorsal roots, particularly one or more target dorsal root ganglions (DRGs). In some embodiments, the system 110 is used to sense signals propagating towards one or more target DRG, propagating away from one or more target DRG and/or within the one or more target DRG. Each target DRG is connected between adjacent distal sensory nerve fibers and adjacent proximal sensory nerve fibers. The adjacent distal sensory nerve fibers propagate electrical signals from a periphery of the patient toward the target DRG. The adjacent proximal sensory nerve fibers propagate electrical signals away from the target DRG toward a central nervous system of the patient.

In some embodiments, the system 110 is used to sense a signal indicative of an electrical field resulting from an electrical signal propagated by adjacent distal sensory nerve fibers toward a target DRG. The sensed signal indicative of an electrical field resulting from an electrical signal propagated by adjacent distal sensory nerve fibers toward a target DRG will often be referred to herein as an a "sensed input signal" or simply an "input signal", since this signal corresponds to a signal being input to the target DRG.

Additionally, or alternatively, the system 110 is used to sense a signal indicative of an electrical field resulting from an electrical signal propagated by adjacent proximal sensory nerve fibers away from a target DRG toward a central nervous system of the patient. The sensed signal indicative of an electrical field resulting from an electrical signal propagated by adjacent proximal sensory nerve fibers away from a target DRG toward a central nervous system of the patient will often be referred to herein as a "sensed output signal" or simply an "output signal", since this signal corresponds to a signal being output from the target DRG.

Additionally, or alternatively, the system 110 is used to sense a signal indicative of an electrical field produced by cell bodies of primary sensory neurons within the target DRG and resulting from an electrical signal propagated by sensory nerve fibers within the target DRG. The sensed signal indicative of an electrical field produced by cell bodies of primary sensory neurons within the target DRG and resulting from an electrical signal propagated by sensory nerve fibers within the target DRG will often be referred to as a "DRG signal", since this signal corresponds to a signal within the DRG.

Figure 2:
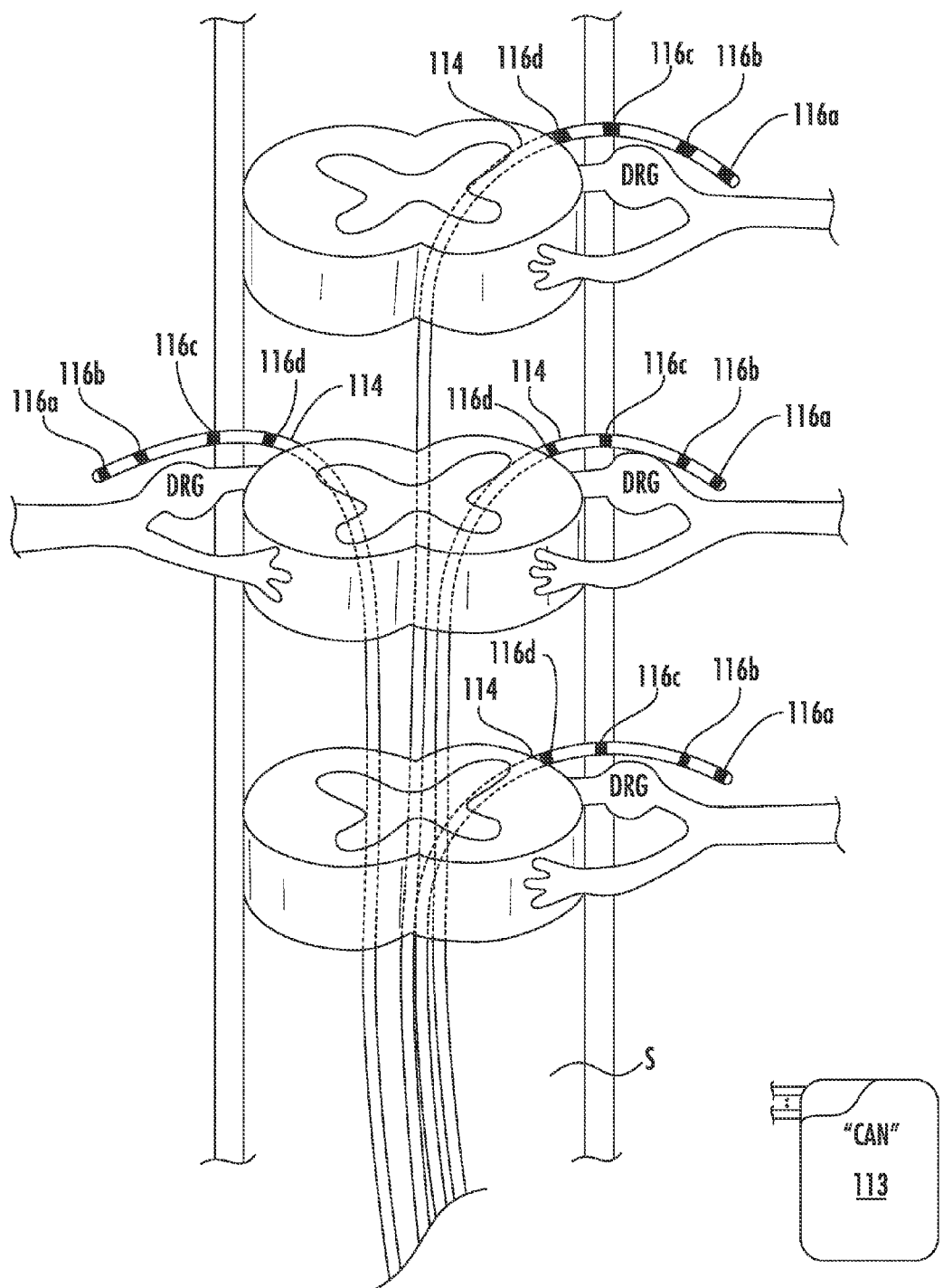
FIG. 2 illustrates example placement of the leads shown in FIG. 1A within the patient anatomy.

FIG. 2 illustrates example placement of the leads 114 of the system 110 within the patient anatomy. In this example, each lead 114 is individually advanced within the spinal column S in an antegrade direction, however other approaches are possible and encompassed by embodiments described herein. Each lead 114 has a distal end which is guidable toward a target DRG and positionable so that one or more of its electrodes 116 are in proximity to the target DRG. In particular, FIG. 2 illustrates four leads 114 having electrodes 116 that are in proximity to four target DRGs. These four target DRGs are located on three levels, wherein two of the target DRGs are on the same level. It may be appreciated that any number of target DRGs and any combination of target DRGs may be stimulated and or sensed with the system 110. It may also be appreciated that more than one lead 114 may be positioned so as to stimulate and/or sense signals associated with an individual target DRG. Exemplary sensing vectors, that can be used to obtain the above described input, output and DRG signals will now be described with reference to FIG. 2.

In accordance with certain embodiments, a lead 114 is positioned relative to a target DRG such that two electrodes (e.g., 116b and 116c) straddle the target DRG, another electrode (e.g., 116a) is near distal sensory nerve fibers that propagate signals toward the target DRG, and a further electrode (e.g., 116d) is near proximal sensory nerve fibers that propagate signals away from the target DRG toward the central nervous system of the patient. The term near, as used herein, means as close as reasonably possible to a specified anatomical location (e.g., a target DRG, distal sensory nerve fibers that propagate signals toward the target DRG, or proximal sensory nerve fibers that propagate signals away from the target DRG), including on (i.e., touching), about or adjacent the specified anatomical location, but in general means within about 5 mm of the specified anatomical location, and more preferably within about 1-2 mm of the specified anatomical location.

By positing a lead 114 as described above and shown in FIG. 2, the two electrodes (e.g., 116b and 116c) of the lead 114 that straddle the target DRG can be used to sense, and more generally obtain, a DRG signal indicative of an electrical field produced by cell bodies of primary sensory neurons within the target DRG and resulting from an electrical signal propagated by sensory nerve fibers within the target DRG. In other words, the DRG signal can be obtained using a sensing vector between electrodes 116b and 116c. Alternatively, the DRG signal can be obtained using a sensing vector between one electrode (e.g., 116b or 116c) of the lead and the electrically conductive device housing 113 (i.e., the "can").

By positing a lead 114 as described above and shown in FIG. 2, two electrodes (e.g., 116a and 116b) of the lead 114 can be used to sense, and more generally obtain, an input signal indicative of an electrical field resulting from an electrical signal propagated by the adjacent distal sensory nerve fibers toward the target DRG. In other words, the input signal can be obtained using a sensing vector between electrodes 116a and 116b. Alternatively, the input signal can be obtained using a sensing vector between one electrode (e.g., 116a) of a lead 114 and the electrically conductive device housing 113 (i.e., the "can").

Referring again to FIG. 2, by positing a lead 114 as described above and shown in FIG. 2, two electrodes (e.g., 116d and 116c) of the lead 114 can be used to sense, and more generally obtain, an output signal indicative of an electrical field resulting from an electrical signal propagated by the adjacent proximal sensory nerve fibers away from the target DRG toward the central nervous system of the patient. In other words, the output signal can be obtained using a sensing vector between electrodes 116d and 116c. Alternatively, the output signal can be obtained using a sensing vector between one electrode (e.g., 116d) of a lead 114 and the electrically conductive device housing 113 (i.e., the "can").

Exemplary Methods

As will be described in additional detail below, with reference to the flow diagram of FIG. 3, certain embodiments of the present invention analyze one or more of the aforementioned input, output and DRG signals, and selectively turn on and off delivery of the electrical stimulation to a target DRG based on results of the analysis. Additionally, or alternatively, certain embodiments of the present invention analyze one or more of the aforementioned input, output and DRG signals, and adjust neurostimulation parameters (e.g., a pulse amplitude, a pulse width and/or a pulse repetition rate) based on results of the analysis.

Figure 3:
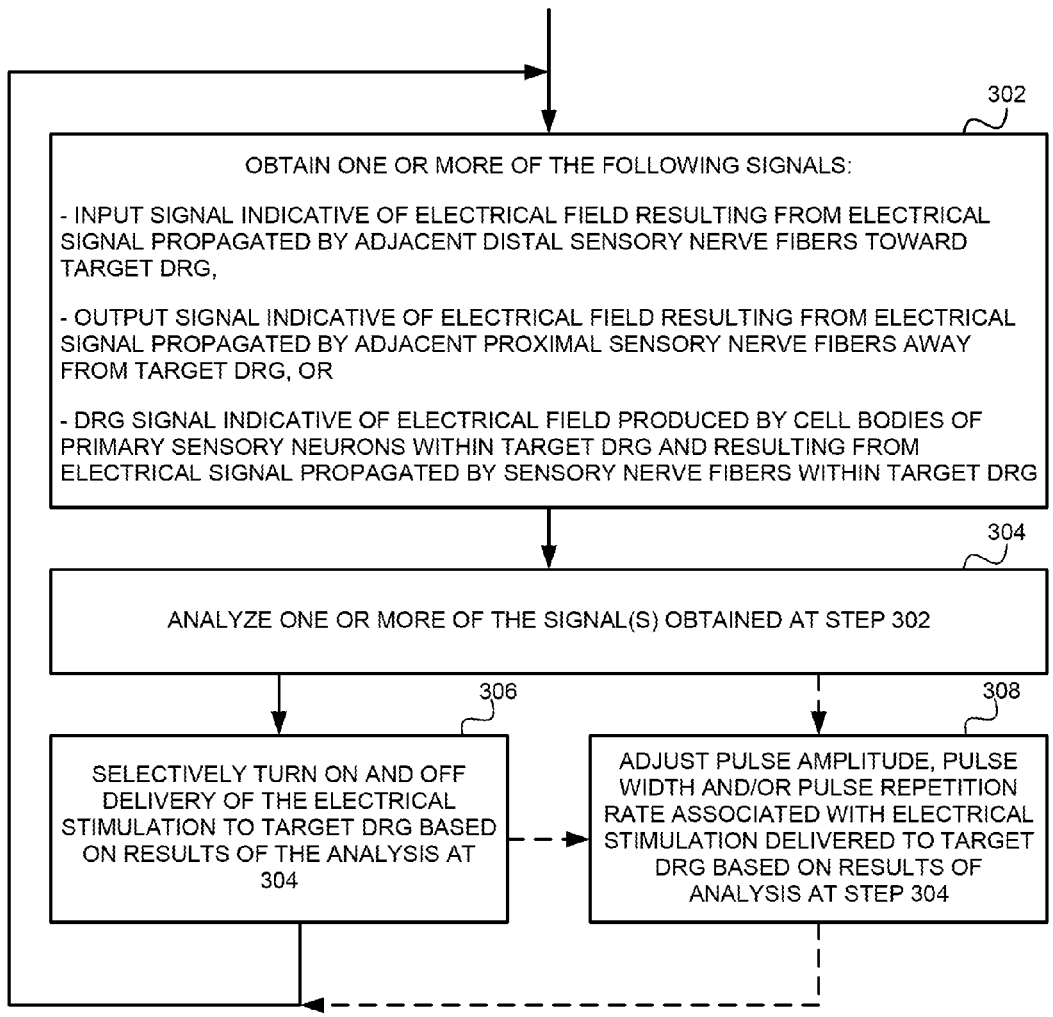
FIG. 3 is a high level flow diagram that is used to summarize methods according to various embodiments of the present invention.

Referring to FIG. 3, at step 302, at least one of the one or more electrodes 116 of the one or more leads 114 are used to obtain at least one of: an input signal indicative of an electrical field resulting from an electrical signal propagated by the adjacent distal sensory nerve fibers toward the target DRG; an output signal indicative of an electrical field resulting from an electrical signal propagated by the adjacent proximal sensory nerve fibers away from the target DRG; or a DRG signal indicative of an electrical field produced by cell bodies of primary sensory neurons within the target DRG and resulting from an electrical signal propagated by sensory nerve fibers within the target DRG. As mentioned above, such signals can be referred to, respectively, as an input signal, an output signal and a DRG signal. Accordingly, at step 302, at least one of an input signal, an output signal or a DRG signal are obtained.

At step 304, at least one of the one or more signals obtained at step 302 are analyzed. At step 306, delivery of electrical stimulation to the target DRG is selectively turned on and off based on results of the analyzing at 304. Additionally, or alternatively, at step 308, at least one of a pulse amplitude, a pulse width or a pulse repetition rate associated with electrical stimulation delivered to the target DRG is adjusted based on the results of the analyzing at step 308. In specific embodiments where both steps 306 and 308 are performed, step 308 is only performed when delivery of electrical stimulation is turned on at step 306.

The aforementioned input, output and/or DRG signals are preferably obtained in a manner that prevents such signals from including artifacts of electrical stimulation delivered to the target DRG. This can be achieved by only obtaining such signals during specific windows of time where it is expected that stimulation artifacts have already dissipated. Additionally, where an output signal and/or a DRG signal is being obtained, for the purpose of determining whether stimulation of the target DRG successfully reduced a level of pain perception, the window of time during which the output signal and/or DRG signal is/are obtained should be close enough in time to the delivered electrical stimulation of the target DRG such that the patient's reduction in the level pain perception is still being experienced. In other words, the beginning of the window of time (during which an output signal and/or a DRG signal is/are obtained) should begin after stimulation artifacts have already dissipated, and should end before the reduction in the level pain perception has diminished. Parameters that define such windows of time, which can be identified for a patient population through experimentation and/or on a patient by patient basis through experimentation, can be programmed into an INS.

Where there is a desire to obtain an input signal, an output signal and/or a DRG signal during a period of time that electrical stimulation of the target DRG is turned on, depending on the stimulation frequency, there may be a need to temporarily interrupt such electrical stimulation for one or more brief periods of time, so that the obtained signal(s) and the sensing circuitry used for obtaining such signal(s) is/are not swamped or saturated by the electrical stimulation. In other words, the input, output and/or DRG signals are preferably obtained in a manner that prevents such signals from including artifacts of electrical stimulation delivered to the target DRG. Additionally, the input, output and/or DRG signals are preferably obtained in a manner that prevents saturation of the sensing circuitry (e.g., 133). For the purpose of this description, such a temporary interruption of electrical stimulation of a target DRG (where the interruption is for the purpose of enabling an input signal, an output signal and/or a DRG signal to be obtained) is not considered to be turning off the electrical stimulation of the target DRG, and preferably occurs for a period that is brief enough that a patient does not notice any interruption in their pain relief. Each such temporarily interruption of electrical stimulation, which can also be referred to as a sensing period, should be for less than 10 seconds, and is preferably for less than 1 second, and more preferably for less than 100 milliseconds. More generally, once a patient is experiencing pain relief as a result of electrical stimulation of a target DRG, after the electrical stimulation is stopped it typically takes a least some amount of time before the perception of pain returns. Preferably, the temporarily interruption of electrical stimulation (i.e., the sensing period) should be short enough such that the perception of pain does not have a chance to return. By contrast, if electrical stimulation of a target DRG is stopped for the purpose of reducing power consumption, this is considered to be turning off the electrical stimulation of the target DRG. If an input signal, an output signal and/or a DRG signal is/are obtained while the electrical stimulation of the target DRG is already turned off to conserve power, there is no need to perform the just described temporary interruption of electrical stimulation.

Analysis of Both Output and Input Signals

Still referring to FIG. 3, in accordance with certain embodiments, at step 302, both the input signal and the output signal are obtained. In such embodiments, step 304 can include comparing the output signal to the input signal, and step 306 can include selectively turning on and off delivery of the electrical stimulation to the target DRG based on results of the comparing at step 304.

In certain embodiments, step 304 can include determining an input metric indicative of how many pulses occur during a specified time period (e.g., a time period between 250 ms and 500 ms, inclusive, but not limited thereto) of the input signal, determining an output metric indicative of how many pulses occur during a specified time period (e.g., 100 ms) of the output signal, and comparing the output metric and input metric to one another. Such metrics can be determined, e.g., by counting a number of peaks, threshold crossings, zero crossings or inflection points that occur during the specified period (e.g., 100 ms) of the signal of interest, but is not limited thereto. It is expected that the DRG may act as a modulator, and that where stimulation of a target DRG successfully reduces a level of pain perception to an acceptable level, the number of pulses during a time period of the output signal will be less than the number of pulses during a same time period of the input signal. Conversely, it is expected that where stimulation of a target DRG does not successfully reduce the level of pain perception to an acceptable level, the number of pulses during a time period of the output signal will be substantially the same as or greater than the number of pulses during a same time period of the input signal. Accordingly, in certain embodiments, at step 306 stimulation of the target DRG is turned off (or kept off) whenever the output metric (indicative of how many pulses occur during a specified time period, e.g., 100 ms, of the output signal) is at least a threshold amount less than the input metric (indicative of how many pulses occur during a specified time period, e.g., 100 ms, of the input signal). Conversely, at step 306 stimulation of the target DRG can be turned on (or kept on) whenever the output metric (indicative of how many pulses occur during a specified time period, e.g., 100 ms, of the output signal) is not at least the threshold amount less than the input metric (indicative of how many pulses occur during a specified time period, e.g., 100 ms, of the input signal). The aforementioned pulses can be relatively narrow spikes, or wider types of pules.

The threshold amount can specify a predetermined number of pulses (e.g., 10 pulses), or a predetermined percentage (e.g., 50%), but is not limited thereto. For another example, a ratio of the output metric to the input metric can be determined and compared to a threshold ratio (e.g., 1:2), and stimulation of the target DRG can be turned off (or kept off) at step 306 whenever the determined ratio falls below the threshold ratio. Conversely, stimulation of the target DRG can be turned on (or kept on) at step 306 whenever the determined ratio is above the threshold ratio.

One or more of the aforementioned or below mentioned thresholds, which can be determined for a patient population through experimentation and/or on a patient by patient basis through experimentation, can be programmed into an INS. For a more specific example, various levels of stimulation can be delivered to a target DRG until the patient indicates that their level of pain perception has been reduced from an unacceptable level to an acceptable level, and one or more thresholds can be calibrated to correspond to that point. What is deemed an acceptable level of pain perception may differ from patient to patient. For example, some patients may consider a level of pain perception corresponding to a visual analogue scale (VAS) score of 2 to be acceptable, whereas other patients may consider a level of pain perception corresponding to a VAS score of 3 to be acceptable. By calibrating a threshold to a patient, the patient can be provided with an acceptable level of pain relief.

In certain embodiments, where both the input signal and the output signal are obtained at step 302, step 304 can include determining an input metric indicative of an amplitude of pulses of the input signal, determining an output metric indicative of an amplitude of pulses of the output signal, and comparing such output and input metrics to one another. For example, the amplitude of pulses of the input signal that occur during the specified period (e.g., 100 ms) can be measured and then averaged, added, or otherwise combined. Similarly the amplitude of pulses of the output signal that occur during the specified period (e.g., 100 ms) can be measured and then averaged, added, or otherwise combined. If a DRG operates like an amplifier, it may be that the amplitude of pulses of the output signal will normally be greater than the amplitude of pulses of the input signal, with the difference in such amplitudes increasing the more the patient perceives pain. Assuming the DRG operates like an amplifier, it is expected that where stimulation of a target DRG successfully reduces a level of pain perception to an acceptable level, the amplitude of pulses of the output signal will be reduced compared to the amplitude of pulses of the output signal where stimulation of the target DRG fails to successfully reduce the level of pain perception to an acceptable level. If a DRG operates more like a filter than an amplifier, it is expected that where stimulation of a target DRG successfully reduces a level of pain perception to an acceptable level, the amplitude of pulses of the output signal will be less than the amplitude of pulses of the input signal. Conversely, still assuming the DRG operates like a filter, it is expected that where stimulation of a target DRG does not successfully reduce the level of pain perception to an acceptable level, the amplitude of pulses of the output signal will not be significantly less than the amplitude of pulses of the input signal. Accordingly, in certain embodiment, at step 306 stimulation of the target DRG is turned off (or kept off) whenever the output metric (indicative of an amplitude of pulses of the output signal) is at least a threshold amount less than the input metric (indicative of an amplitude of pulses of the input signal). Conversely, stimulation of the target DRG can be turned on (or kept on) whenever the output metric (indicative of an amplitude of pulses of the output signal) is not at least the threshold amount less than the input metric (indicative of an amplitude of pulses of the input signal). This threshold amount can specify a predetermined value (e.g., 10 microvolts, but not limited thereto), or a predetermined percentage (e.g., 50%), but is not limited thereto. For another example, a ratio of the output metric to the input metric can be determined and compared to a threshold ratio (e.g., 1:2), and stimulation of the target DRG can be selectively turned off and on at step 306 in dependence on whether the ratio falls below the threshold ratio. In a similar manner as was discussed above, such a threshold can be calibrated for a specific patient and programmed into the INS.

Alternatively, or additionally, where both the input signal and the output signal are obtained at step 302, step 304 can include determining an input metric indicative of a width of pulses of the input signal, determining an output metric indicative of a width of pulses of the output signal, and comparing such output and input metrics to one another. For example, the width of pulses of the input signal that occur during the specified period (e.g., 100 ms) can be measured and then averaged, added, or otherwise combined. Similarly the width of pulses of the output signal that occur during the specified period (e.g., 100 ms) can be measured and then averaged, added, or otherwise combined.

It may be the case that where stimulation of a target DRG successfully reduces a level of pain perception to an acceptable level, the width of pulses of the output signal will be less than the width of pulses of the input signal. Conversely, it is expected that where stimulation of a target DRG does not successfully reduce the level of pain perception to an acceptable level, the width of pulses during a time period of the output signal will be substantially the same as or greater than the width of pulses during the input signal. Accordingly, in certain embodiment, at step 306 stimulation of the target DRG is turned off (or kept off) whenever the output metric (indicative of the width of pulses of the output signal) is at least a threshold amount less than the input metric (indicative of the width of pulses of the input signal). Such a threshold amount can specify a predetermined value (e.g., a value between 10 $\mu$s and 100 $\mu$s, inclusive, but not limited thereto), or a predetermined percentage (e.g., 50%), but is not limited thereto. Conversely, stimulation of the target DRG can be turned on (or kept on) whenever the output metric (indicative of the width of pulses of the output signal) is not at least the threshold amount less than the input metric (indicative of the width of pulses of the input signal). For another example, a ratio of the output metric to the input metric can be determined and compared to a threshold ratio (e.g., 1:2), and stimulation of the target DRG can be selectively turned off and on at step 306 in dependence on whether the determined ratio falls below the threshold ratio.

Alternatively, or additionally, where both the input signal and the output signal are obtained at step 302, step 304 can include determining the area under (or integration of) a period (e.g., 100 ms) of the input signal, the area under (or integration of) a period (e.g., 100 ms) of the output signal, and comparing the area (or integration result) of the output signal to the area (or integration result) of the input signal.

It is expected that where stimulation of a target DRG successfully reduces a level of pain perception to an acceptable level, the area under (or integration of) a period (e.g., 100 ms) of the output signal will be less than the area under (or integration of) a period (e.g., 100 ms) of the input signal. Conversely, it is expected that where stimulation of a target DRG does not successfully reduce the level of pain perception to an acceptable level, the area under (or integration of) a period (e.g., 100 ms) of the output signal will be substantially that same as or greater than the area under (or integration of) a period (e.g., 100 ms) of the input signal. Accordingly, in certain embodiments, at step 306 stimulation of the target DRG is turned off (or kept off) whenever the output metric (indicative of the area under or integration of a period of the output signal) is at least a threshold amount less than the input metric (indicative of the area under or integration of a period of input signal). Conversely, stimulation of the target DRG can be turned on (or kept on) whenever the output metric (indicative of the area under or integration of a period of the output signal) is not at least a threshold amount less than the input metric (indicative of the area under or integration of a period of input signal).

In certain embodiments, once the stimulation of the target DRG is turned off, it is not turned back on until the reason for turning off the stimulation is no longer satisfied. For example, if the stimulation of the target DRG was turned off because output metric dropped below the input metric by at least the threshold amount, the stimulation of the target DRG is turned back on once the output metric is no longer below the input metric by at least the threshold amount. In this manner, steps 302, 304 and 306 can be repeated over time to thereby enable the selective turning on and off of stimulation of the target DRG based on closed loop feedback. In certain embodiments, hysteresis thresholding can be used, to limit how often stimulation of a target DRG is turned on and off. In other words, different thresholds can be used for turning stimulation on and turning stimulation off.

The aforementioned embodiments can be combined. For example, more than one type of metric can be determined for each of the sensed input and output signals. Corresponding metrics can be compared to one another and/or to appropriate thresholds. Alternatively, metrics of a sensed signal can be combined (e.g., using weighting factors and/or algorithms) and the resulting combined metrics can be compared to one another and/or or to appropriate thresholds.

In certain embodiments, once the stimulation of the target DRG is turned off, it remains off for a predetermined programmed period of time (e.g., 30 minutes), after which stimulation of the target DRG is automatically turned back on.

In other embodiments, once the stimulation of the target DRG is turned off, it remains off for at least a predetermined programmed period of time (e.g., 10 minutes), after which stimulation of the target DRG is turned back on if/once the reason for turning off the stimulation is no longer satisfied. For example, if the reason for turning off the stimulation is no longer satisfied when the predetermined programmed period of "off" time (e.g., 10 minutes) ends, then stimulation of the target DRG is resumed as soon as the predetermined programmed period of "off" time (e.g., 10 minutes) ends. On the other hand, if the reason for turning off the stimulation is still satisfied when the predetermined programmed period of "off" time (e.g., 10 minutes) ends, then stimulation of the target DRG is not resumed until the reason for turning off the stimulation is no longer satisfied.

In accordance with certain embodiments, at step 308 at least one of a pulse amplitude, a pulse width or a pulse repetition rate associated with electrical stimulation delivered to the target DRG is adjusted based on the results of comparing the output signal to the input signal at step 304. For example, where stimulation of a target DRG for at least a period of time using pulses having a first amplitude level does not cause a metric of the output signal to be at least a threshold amount less than a corresponding metric of the input signal, the amplitude of the stimulation pulses can be increased to a second (higher) amplitude level. The amount by which the amplitude is increased can be a fixed amount, or a percentage, but is not limited thereto. Where stimulation of a target DRG does cause a metric of the output signal to be at least a threshold amount less than a corresponding metric of the input signal, in order to reduce power consumption, the amplitude of the stimulation pulses can be decreased to a lower amplitude level. Stimulation of a target DRG at the lower amplitude level can continue for a period of time, after which, the amplitude level of the stimulation pulses can again be decreased (if the metric of the output signal is still at least a threshold amount less than a corresponding metric of the input signal) in order to further reduce power consumption, or can be increased (if the metric of the output signal is no longer at least the threshold amount less than a corresponding metric of the input signal). In this manner, the amplitude of stimulation pulses can be automatically adjusted based on closed loop feedback. The pulse width and/or pulse repetition rate of stimulation pulses can additionally, or alternatively, be automatically adjusted using closed loop feedback that includes comparisons of metrics of the output and input signals.

Analysis of DRG Signal

In certain embodiments, only the DRG signal (indicative of an electrical field produced by cell bodies of primary sensory neurons within the target DRG and resulting from an electrical signal propagated by sensory nerve fibers within the target DRG) is obtained at step 302, and the analyzing of the DRG signal at step 304 includes determining one or more metric of the DRG signal and comparing the metric(s) to one or more corresponding threshold(s). In such embodiments, at step 306, delivery of the electrical stimulation to the target DRG is selectively turned on and off based on results of the analyzing (which includes a comparison) performed at 304. Alternatively, or additionally, at step 308 least one of a pulse amplitude, a pulse width or a pulse repetition rate associated with electrical stimulation delivered to the target DRG is adjusted based on the results of the analyzing at 304. In specific embodiments where both steps 306 and 308 are performed, step 308 is only performed when delivery of electrical stimulation is turned on.

It is expected that where electrical stimulation of a target DRG successfully reduces a patient's level of pain perception to an acceptable level, the number of pulses that occur during a specified time period (e.g., 100 ms) of a sensed DRG signal will be lower than compared to when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, step 304 can include determining a DRG metric indicative of how many pulses occur during a specified time period (e.g., 100 ms) of a sensed DRG signal, and comparing the DRG metric to a corresponding threshold. Such a DRG metric can be determined by counting a number of peaks, threshold crossings, zero crossings or inflection points that occur during a specified period (e.g., 100 ms) of the sensed DRG signal, but is not limited thereto. In such embodiments, stimulation of the target DRG can be turned off (or kept off) whenever the determined DRG metric falls below a specified threshold, or is reduced by at least a specified threshold amount. Conversely, stimulation of the target DRG can be turned on (or kept on) whenever the determined DRG metric is not below the specified threshold, or is not reduced by at least the specified threshold amount. The threshold amount can specify a predetermined number of pulses (e.g., 10 pulses), or a predetermined percentage (e.g., 50%), but is not limited thereto. As explained above, such one or more threshold(s) can be determined for a patient population through experimentation and/or on a patient by patient basis through experimentation, and can be programmed into an INS.

It is expected that where electrical stimulation of a target DRG successfully reduces a patient's level of pain perception to an acceptable level, the amplitude of pulses of a sensed DRG signal will be lower than compared to when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, step 304 can include determining a DRG metric indicative of an amplitude of pulses of a sensed DRG signal, and comparing the DRG metric to a corresponding threshold. The DRG metric indicative of an amplitude of pulses of the sensed DRG signal can be determined, for example, by measuring the amplitude of pulses that occur during a specified time period (e.g., 100 ms) of the DRG signal and then averaging, adding, or otherwise combining the measurements. Accordingly, in certain embodiments, at step 306 stimulation of the target DRG is turned off (or kept off) whenever the DRG metric (indicative of an amplitude of pulses of a sensed DRG signal) falls below a corresponding threshold, or is reduced by at least a corresponding threshold amount. Conversely, stimulation of the target DRG can be turned on (or kept on) whenever the DRG metric (indicative of an amplitude of pulses of the sensed DRG signal) does not fall below the corresponding threshold, or is not reduced by at least the corresponding threshold amount. As explained above, such one or more threshold(s) can be determined for a patient population through experimentation and/or on a patient by patient basis through experimentation, and can be programmed into an INS.

It is expected that where electrical stimulation of a target DRG successfully reduces a patient's level of pain perception to an acceptable level, the width of pulses of a sensed DRG signal will be shorter than compared to when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, step 304 can include determining a DRG metric indicative of a width of pulses of a sensed DRG signal, and comparing the DRG metric to a corresponding threshold. For example, the width of pulses of the DRG signal that occur during a specified period (e.g., 100 ms) can be measured and then averaged, added, or otherwise combined. Stimulation of the target DRG can be selectively turned off and on in dependence on whether the DRG metric (indicative of a width of pulses of a sensed DRG signal) falls below a corresponding threshold, or is reduced by at least a corresponding threshold amount, in similar manners as were discussed above.

Alternatively, or additionally, where a DRG signal is obtained at step 302, step 304 can include analyzing the morphology of the sensed DRG signal. For example, during a calibration procedure, a first morphological template of the DRG signal corresponding to the DRG signal when the patient's level of pain perception is at an unacceptable level can be obtained and stored, and a second morphological template of the DRG signal corresponding to the DRG signal when the patient's level of pain perception is at an acceptable level can be obtained and stored. Thereafter, the morphology of a sensed DRG signal can be compared to the two templates, e.g., using correlation or other template matching techniques, but is not limited thereto. In certain embodiments, if the morphology of the sensed DRG signal is closer to the second template than the first template, then stimulation of a target DRG is turned off (or kept off). Conversely, if the morphology of the sensed DRG signal is closer to the first template than the second template, then stimulation of a target DRG is turned on (or kept on). In other embodiments, the only template obtained and stored is a template corresponding to the DRG signal when the patient's level of pain perception is at an acceptable level. In such embodiments, if the morphology of a sensed DRG signal is within a threshold level of the template, then stimulation of a target DRG is turned off (or kept off). Conversely, if the morphology of the sensed DRG signal is not within the threshold level of the template, then stimulation of the target DRG is turned on (or kept on).

Alternatively, or additionally, where a DRG signal is obtained at step 302, step 304 can include analyzing frequency content of the DRG signal. For example, during a calibration procedure, first information indicative of frequency content of the DRG signal corresponding to the DRG signal when the patient's level of pain perception is at an unacceptable level can be obtained and stored, and second information indicative of frequency content of the DRG signal when the patient's level of pain perception is at an acceptable level can be obtained and stored. Thereafter, the frequency content of a sensed DRG signal can be compared to the saved first and second frequency content information. In certain embodiments, if the frequency content of the sensed DRG signal is closer to the second information (indicative of frequency content of the DRG signal corresponding to the DRG signal when the patient's level of pain perception is reduced to an acceptable level), then stimulation of a target DRG is turned off (or kept off). Conversely, if the frequency content of the sensed DRG signal is closer to the first information (indicative of frequency content of the DRG signal corresponding to the DRG signal when the patient's level of pain perception is at an unacceptable level), then stimulation of a target DRG is turned on (or kept on). In other embodiments, the only DRG frequency content information obtained and stored is information indicative of the frequency content of the DRG signal when the patient's level of pain perception is at an acceptable level. In such embodiments, if the frequency content of a sensed DRG signal is within a threshold level of the stored frequency content information, then stimulation of a target DRG is turned off (or kept off). Conversely, if the frequency content of the sensed DRG signal is not within the threshold level of the stored frequency content information, then stimulation of the target DRG is turned on (or kept on). The aforementioned frequency content can be determined for a sensed DRG signal using one or more filters and or using one or more mathematical transforms, but is not limited thereto.

Alternatively, or additionally, where a DRG signal is obtained at step 302, step 304 can include determining the area under (or integration of) a period (e.g., 100 ms) of the DRG signal, and comparing the area (or integration result) of the DRG signal to a corresponding threshold. It is expected that where stimulation of a target DRG successfully reduces a level of pain perception to an acceptable level, the area under (or integration of) a period (e.g., 100 ms) of the DRG signal will be less than when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, at step 306 stimulation of the target DRG is turned off (or kept off) whenever the DRG metric (indicative of the area under or integration of a period of the output signal) falls below a corresponding threshold, or is reduced by at least a corresponding threshold amount, in similar manners as were discussed above. Conversely, stimulation of the target DRG can be turned on (or kept on) whenever the DRG metric (indicative of the area under or integration of a period of the output signal) is not below the corresponding threshold, or is not reduced by at least the corresponding threshold amount, in similar manners as were discussed above.

The aforementioned embodiments can be combined. For example, more than one type of metric can be determined for a sensed DRG signal. Each metric can be compared to an appropriate threshold. Alternatively, metrics of a sensed DRG signal can be combined (e.g., using weighting factors and/or algorithms) and the resulting combined metric can be compared to an appropriate threshold.

In a similar manner as was discussed above, in certain embodiments, once the stimulation of the target DRG is turned off, it is not turned back on until the reason for turning off the stimulation is no longer satisfied. For example, if the stimulation of the target DRG was turned off because a DRG metric dropped below a corresponding threshold, the stimulation of the target DRG is turned back on once the DRG metric is no longer below the corresponding threshold. In this manner, steps 302, 304 and 306 can be repeated over time to thereby enable the selective turning on and off of stimulation of the target DRG based on closed loop feedback. In certain embodiments, hysteresis thresholding can be used, to limit how often stimulation of a target DRG is turned on and off. In other words, different thresholds can be used for turning stimulation on and turning stimulation off.

In certain embodiments, once the stimulation of the target DRG is turned off, it remains off for a predetermined programmed period of time (e.g., 30 minutes), after which stimulation of the target DRG is automatically turned back on.

In other embodiments, once the stimulation of the target DRG is turned off, it remains off for at least a predetermined programmed period of time (e.g., 10 minutes), after which stimulation of the target DRG is turned back on if/once the reason for turning off the stimulation is no longer satisfied. For example, if the reason for turning off the stimulation is no longer satisfied when the predetermined programmed period of "off" time (e.g., 10 minutes) ends, then stimulation of the target DRG is resumed as soon as the predetermined programmed period of "off" time (e.g., 10 minutes) ends. On the other hand, if the reason for turning off the stimulation is still satisfied when the predetermined programmed period of "off" time (e.g., 10 minutes) ends, then stimulation of the target DRG is not resumed until the reason for turning off the stimulation is no longer satisfied.

In accordance with certain embodiments, at step 308 at least one of a pulse amplitude, a pulse width or a pulse repetition rate associated with electrical stimulation delivered to the target DRG is adjusted based on the results of comparing one or more metric of a sensed DRG signal to one or more corresponding threshold. For example, where stimulation of a target DRG for at least a period of time using pulses having a first amplitude level does not cause a metric of a sensed DRG signal to fall below a corresponding threshold, or be reduced by at least a threshold amount, then the amplitude of the stimulation pulses can be increased to a second (higher) amplitude level. The amount by which the amplitude is increased can be a fixed amount, or a percentage, but is not limited thereto. If stimulation of a target DRG does cause a metric of the sensed DRG signal to fall below the corresponding threshold, or be reduced by at least the threshold amount, then (in order to reduce power consumption) the amplitude of the stimulation pulses can be decreased to a lower amplitude level. Stimulation of a target DRG at the lower amplitude level can continue for a period of time, after which, the amplitude level of the stimulation pulses can again be decreased (if the metric of the sensed DRG signal is still below the corresponding threshold) or can be increased (if the metric of the sensed DRG signal is no longer below the threshold). In this manner, the amplitude of stimulation pulses can be automatically adjusted based on closed loop feedback. The pulse width and/or pulse repetition rate of stimulation pulses can additionally, or alternatively, be automatically adjusted using closed loop feedback that includes comparisons of metrics of a sensed DRG to one or more thresholds.

In accordance with certain embodiments, at step 308 at least one of a pulse amplitude, a pulse width or a pulse repetition rate associated with electrical stimulation pulses delivered to the target DRG is adjusted based on results of comparing the morphology of a sensed DRG signal to a first morphological template (corresponding to the DRG signal when the patient's level of pain perception is at an unacceptable level) and a second morphological template (corresponding to the DRG signal when the patient's level of pain perception is at an acceptable level). Exemplary details of how such templates can be obtained and stored are discussed above. The morphology of a sensed DRG signal can be compared to the two templates, e.g., using correlation or other template matching techniques, but is not limited thereto. In certain embodiments, if the morphology of the sensed DRG signal is closer to the first template than the second template, then the pulse amplitude can be increased (alternatively, or additionally, the pulse width and/or pulse repetition rate can be increased). Conversely, if the morphology of the sensed DRG signal is closer to the second template than the first template, then the pulse amplitude can be decreased (alternatively, or additionally, the pulse width and/or pulse repetition rate can be decreased). In other embodiments, the only template obtained and stored is a template corresponding to the DRG signal when the patient's level of pain perception is at an acceptable level. In such embodiments, if the morphology of a sensed DRG signal is not within a threshold level of the template, then the pulse amplitude can be increased (alternatively, or additionally, the pulse width and/or pulse repetition rate can be increased). Conversely, if the morphology of the sensed DRG signal is within the threshold level of the template, then the pulse amplitude can be decreased to attempt to reduce power consumption (alternatively, or additionally, pulse width and/or pulse repetition rate can be decreased).

In still other embodiments, one or more of pulse amplitude, pulse width or pulse repetition rate are adjusted in a closed loop manner to cause the morphology of a sensed DRG signal to be within a threshold level of the morphological template corresponding to the DRG signal when the patient's level of pain perception is at an acceptable level.

In accordance with certain embodiments, at step 308 at least one of a pulse amplitude, a pulse width or a pulse repetition rate associated with electrical stimulation pulses delivered to the target DRG is adjusted based on results of comparing frequency content of a sensed DRG signal to first frequency content information (corresponding to the DRG signal when the patient's level of pain perception is at an unacceptable level) and second frequency content information (corresponding to the DRG signal when the patient's level of pain perception is at an acceptable level can be obtained and stored). Exemplary details of how such frequency content information can be obtained and stored are discussed above. The frequency content of a sensed DRG signal can be compared to the first and second frequency content information. In certain embodiments, if the frequency content of the sensed DRG signal is closer to the first frequency content information (corresponding to the DRG signal when the patient's level of pain perception is at an unacceptable level), then the pulse amplitude can be increased (alternatively, or additionally, the pulse width and/or pulse repetition rate can be increased). Conversely, if the frequency content of the sensed DRG signal is closer to the second frequency content information (corresponding to the DRG signal when the patient's level of pain perception is at an acceptable level), then the pulse amplitude can be decreased (alternatively, or additionally, the pulse width and/or pulse repetition rate can be decreased). In other embodiments, the only frequency content information stored is the frequency content information corresponding to the DRG signal when the patient's level of pain perception is at an acceptable level. In such embodiments, if the frequency content of a sensed DRG signal is not within a threshold level of the stored frequency content information, then the pulse amplitude can be increased (alternatively, or additionally, the pulse width and/or pulse repetition rate can be increased). Conversely, if the frequency content of the sensed DRG signal is within the threshold level of the stored frequency content information, then the pulse amplitude can be decreased to attempt to reduce power consumption (alternatively, or additionally, pulse width and/or pulse repetition rate can be decreased).

In still other embodiments, one or more of pulse amplitude, pulse width or pulse repetition rate are adjusted in a closed loop manner to cause the frequency content of a sensed DRG signal to be within a threshold level of the stored frequency content information corresponding to the DRG signal when the patient's level of pain perception is at an acceptable level.

Analysis of Output Signal

In certain embodiments, only the output signal (indicative of an electrical field resulting from an electrical signal propagated by the adjacent proximal sensory nerve fibers away from the target DRG) is obtained at step 302, and the analyzing of the output signal at step 304 includes determining one or more metric of the output signal and comparing the metric(s) to one or more corresponding threshold(s). In such embodiments, at step 306, delivery of the electrical stimulation to the target DRG is selectively turned on and off based on results of the analyzing (which includes a comparison) performed at 304. Alternatively, or additionally, at step 308 least one of a pulse amplitude, a pulse width or a pulse repetition rate associated with electrical stimulation delivered to the target DRG is adjusted based on the results of the analyzing at 304. In specific embodiments where both steps 306 and 308 are performed, step 308 is only performed when delivery of electrical stimulation is turned on.

It is expected that where electrical stimulation of a target DRG successfully reduces a patient's level of pain perception to an acceptable level, the number of pulses that occur during a specified time period (e.g., 100 ms) of a sensed output signal will be lower than compared to when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, step 304 can include determining a DRG metric indicative of how many pulses occur during a specified time period (e.g., 100 ms) of a sensed output signal, and comparing the DRG metric to a corresponding threshold. Such a DRG metric can be determined by counting a number of peaks, threshold crossings, zero crossings or inflection points that occur during a specified period (e.g., 100 ms) of the sensed output signal, but is not limited thereto. In such embodiments, stimulation of the target DRG can be turned off (or kept off) whenever the determined DRG metric falls below a specified threshold, or is reduced by at least a specified threshold amount. Conversely, stimulation of the target DRG can be turned on (or kept on) whenever the determined DRG metric is not below the specified threshold, or is not reduced by at least the specified threshold amount. The threshold amount can specify a predetermined number of pulses (e.g., 10 pulses), or a predetermined percentage (e.g., 50%), but is not limited thereto. As explained above, such one or more threshold(s) can be determined for a patient population through experimentation and/or on a patient by patient basis through experimentation, and can be programmed into an INS.

It is expected that where electrical stimulation of a target DRG successfully reduces a patient's level of pain perception to an acceptable level, the amplitude of pulses of a sensed output signal will be lower than compared to when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, step 304 can include determining a DRG metric indicative of an amplitude of pulses of a sensed output signal, and comparing the DRG metric to a corresponding threshold. The DRG metric indicative of an amplitude of pulses of the sensed output signal can be determined, for example, by measuring the amplitude of pulses that occur during a specified time period (e.g., 100 ms) of the output signal and then averaging, adding, or otherwise combining the measurements. Accordingly, in certain embodiments, at step 306 stimulation of the target DRG is turned off (or kept off) whenever the DRG metric (indicative of an amplitude of pulses of a sensed output signal) falls below a corresponding threshold, or is reduced by at least a corresponding threshold amount. Conversely, stimulation of the target DRG can be turned on (or kept on) whenever the DRG metric (indicative of an amplitude of pulses of the sensed output signal) does not fall below the corresponding threshold, or is not reduced by at least the corresponding threshold amount. As explained above, such one or more threshold(s) can be determined for a patient population through experimentation and/or on a patient by patient basis through experimentation, and can be programmed into an INS.

It is expected that where electrical stimulation of a target DRG successfully reduces a patient's level of pain perception to an acceptable level, the width of pulses of a sensed output signal will be shorter than compared to when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, step 304 can include determining a DRG metric indicative of a width of pulses of a sensed output signal, and comparing the DRG metric to a corresponding threshold. For example, the width of pulses of the output signal that occur during a specified period (e.g., 100 ms) can be measured and then averaged, added, or otherwise combined. Stimulation of the target DRG can be selectively turned off and on in dependence on whether the DRG metric (indicative of a width of pulses of a sensed output signal) falls below a corresponding threshold, or is reduced by at least a corresponding threshold amount, in similar manners as were discussed above.

Alternatively, or additionally, where a output signal is obtained at step 302, step 304 can include analyzing the morphology of the sensed output signal. For example, during a calibration procedure, a first morphological template of the output signal corresponding to the output signal when the patient's level of pain perception is at an unacceptable level can be obtained and stored, and a second morphological template of the output signal corresponding to the output signal when the patient's level of pain perception is at an acceptable level can be obtained and stored. Thereafter, the morphology of a sensed output signal can be compared to the two templates, e.g., using correlation or other template matching techniques, but is not limited thereto. In certain embodiments, if the morphology of the sensed DRG signal is closer to the second template than the first template, then stimulation of a target DRG is turned off (or kept off). Conversely, if the morphology of the sensed DRG signal is closer to the first template than the second template, then stimulation of a target DRG is turned on (or kept on). In other embodiments, the only template obtained and stored is a template corresponding to the output signal when the patient's level of pain perception is at an acceptable level. In such embodiments, if the morphology of a sensed output signal is within a threshold level of the template, then stimulation of a target DRG is turned off (or kept off). Conversely, if the morphology of the sensed output signal is not within the threshold level of the template, then stimulation of the target DRG is turned on (or kept on).

Alternatively, or additionally, where an output signal is obtained at step 302, step 304 can include analyzing frequency content of the output signal. For example, during a calibration procedure, first information indicative of frequency content of the output signal corresponding to the output signal when the patient's level of pain perception is at an unacceptable level can be obtained and stored, and second information indicative of frequency content of the output signal when the patient's level of pain perception is at an acceptable level can be obtained and stored. Thereafter, the frequency content of a sensed output signal can be compared to the saved first and second frequency content information. In certain embodiments, if the frequency content of the sensed DRG signal is closer to the second information (indicative of frequency content of the output signal corresponding to the output signal when the patient's level of pain perception is reduced to an acceptable level), then stimulation of a target DRG is turned off (or kept off). Conversely, if the frequency content of the sensed DRG signal is closer to the first information (indicative of frequency content of the output signal corresponding to the output signal when the patient's level of pain perception is at an unacceptable level), then stimulation of a target DRG is turned on (or kept on). In other embodiments, the only DRG frequency content information obtained and stored is information indicative of the frequency content of the output signal when the patient's level of pain perception is at an acceptable level. In such embodiments, if the frequency content of a sensed output signal is within a threshold level of the stored frequency content information, then stimulation of a target DRG is turned off (or kept off). Conversely, if the frequency content of the sensed output signal is not within the threshold level of the stored frequency content information, then stimulation of the target DRG is turned on (or kept on). The aforementioned frequency content can be determined for a sensed output signal using one or more filters and or using one or more mathematical transforms, but is not limited thereto.

Alternatively, or additionally, where a output signal is obtained at step 302, step 304 can include determining the area under (or integration of) a period (e.g., 100 ms) of the output signal, and comparing the area (or integration result) of the output signal to a corresponding threshold. It is expected that where stimulation of a target DRG successfully reduces a level of pain perception to an acceptable level, the area under (or integration of) a period (e.g., 100 ms) of the output signal will be less than when the patient is experiencing an unacceptable level of pain (either because the electrical stimulation of the target DRG is not successfully reducing the patient's level of pain perception to an acceptable level, or because there is no electrical stimulation of the target DRG). Accordingly, in certain embodiments, at step 306 stimulation of the target DRG is turned off (or kept off) whenever the DRG metric (indicative of the area under or integration of a period of the output signal) falls below a corresponding threshold, or is reduced by at least a corresponding threshold amount, in similar manners as were discussed above. Conversely, stimulation of the target DRG can be turned on (or kept on) whenever the DRG metric (indicative of the area under or integration of a period of the output signal) is not below the corresponding threshold, or is not reduced by at least the corresponding threshold amount, in similar manners as were discussed above.

The aforementioned embodiments can be combined. For example, more than one type of metric can be determined for a sensed output signal. Each metric can be compared to an appropriate threshold. Alternatively, metrics of a sensed output signal can be combined (e.g., using weighting factors and/or algorithms) and the resulting combined metric can be compared to an appropriate threshold.

In a similar manner as was discussed above, in certain embodiments, once the stimulation of the target DRG is turned off, it is not turned back on until the reason for turning off the stimulation is no longer satisfied. For example, if the stimulation of the target DRG was turned off because a DRG metric dropped below a corresponding threshold, the stimulation of the target DRG is turned back on once the DRG metric is no longer below the corresponding threshold. In this manner, steps 302, 304 and 306 can be repeated over time to thereby enable the selective turning on and off of stimulation of the target DRG based on closed loop feedback. In certain embodiments, hysteresis thresholding can be used, to limit how often stimulation of a target DRG is turned on and off. In other words, different thresholds can be used for turning stimulation on and turning stimulation off.

In certain embodiments, once the stimulation of the target DRG is turned off, it remains off for a predetermined programmed period of time (e.g., 30 minutes), after which stimulation of the target DRG is automatically turned back on.

In other embodiments, once the stimulation of the target DRG is turned off, it remains off for at least a predetermined programmed period of time (e.g., 10 minutes), after which stimulation of the target DRG is turned back on if/once the reason for turning off the stimulation is no longer satisfied. For example, if the reason for turning off the stimulation is no longer satisfied when the predetermined programmed period of "off" time (e.g., 10 minutes) ends, then stimulation of the target DRG is resumed as soon as the predetermined programmed period of "off" time (e.g., 10 minutes) ends. On the other hand, if the reason for turning off the stimulation is still satisfied when the predetermined programmed period of "off" time (e.g., 10 minutes) ends, then stimulation of the target DRG is not resumed until the reason for turning off the stimulation is no longer satisfied.

In accordance with certain embodiments, at step 308 at least one of a pulse amplitude, a pulse width or a pulse repetition rate associated with electrical stimulation delivered to the target DRG is adjusted based on the results of comparing one or more metric of a sensed output signal to one or more corresponding threshold. For example, where stimulation of a target DRG for at least a period of time using pulses having a first amplitude level does not cause a metric of a sensed output signal to fall below a corresponding threshold, or be reduced by at least a threshold amount, then the amplitude of the stimulation pulses can be increased to a second (higher) amplitude level. The amount by which the amplitude is increased can be a fixed amount, or a percentage, but is not limited thereto. If stimulation of a target DRG does cause a metric of the sensed output signal to fall below the corresponding threshold, or be reduced by at least the threshold amount, then (in order to reduce power consumption) the amplitude of the stimulation pulses can be decreased to a lower amplitude level. Stimulation of a target DRG at the lower amplitude level can continue for a period of time, after which, the amplitude level of the stimulation pulses can again be decreased (if the metric of the sensed output signal is still below the corresponding threshold) or can be increased (if the metric of the sensed output signal is no longer below the threshold). In this manner, the amplitude of stimulation pulses can be automatically adjusted based on closed loop feedback. The pulse width and/or pulse repetition rate of stimulation pulses can additionally, or alternatively, be automatically adjusted using closed loop feedback that includes comparisons of metrics of a sensed DRG to one or more thresholds.

In accordance with certain embodiments, at step 308 at least one of a pulse amplitude, a pulse width or a pulse repetition rate associated with electrical stimulation pulses delivered to the target DRG is adjusted based on results of comparing the morphology of a sensed output signal to a first morphological template (corresponding to the output signal when the patient's level of pain perception is at an unacceptable level) and a second morphological template (corresponding to the output signal when the patient's level of pain perception is at an acceptable level). Exemplary details of how such templates can be obtained and stored are discussed above. The morphology of a sensed output signal can be compared to the two templates, e.g., using correlation or other template matching techniques, but is not limited thereto. In certain embodiments, if the morphology of the sensed output signal is closer to the first template than the second template, then the pulse amplitude can be increased (alternatively, or additionally, the pulse width and/or pulse repetition rate can be increased). Conversely, if the morphology of the sensed output signal is closer to the second template than the first template, then the pulse amplitude can be decreased (alternatively, or additionally, the pulse width and/or pulse repetition rate can be decreased). In other embodiments, the only template obtained and stored is a template corresponding to the output signal when the patient's level of pain perception is at an acceptable level. In such embodiments, if the morphology of a sensed output signal is not within a threshold level of the template, then the pulse amplitude can be increased (alternatively, or additionally, the pulse width and/or pulse repetition rate can be increased). Conversely, if the morphology of the sensed output signal is within the threshold level of the template, then the pulse amplitude can be decreased to attempt to reduce power consumption (alternatively, or additionally, pulse width and/or pulse repetition rate can be decreased). In still other embodiments, one or more of pulse amplitude, pulse width or pulse repetition rate are adjusted in a closed loop manner to cause the morphology of a sensed output signal to be within a threshold level of the morphological template corresponding to the output signal when the patient's level of pain perception is at an acceptable level.

In accordance with certain embodiments, at step 308 at least one of a pulse amplitude, a pulse width or a pulse repetition rate associated with electrical stimulation pulses delivered to the target DRG is adjusted based on results of comparing frequency content of a sensed output signal to first frequency content information (corresponding to the output signal when the patient's level of pain perception is at an unacceptable level) and second frequency content information (corresponding to the output signal when the patient's level of pain perception is at an acceptable level are obtained and stored). Exemplary details of how such frequency content information can be obtained and stored are discussed above. The frequency content of a sensed output signal can be compared to the first and second frequency content information. In certain embodiments, if the frequency content of the sensed DRG signal is closer to the first frequency content information (corresponding to the output signal when the patient's level of pain perception is at an unacceptable level), then the pulse amplitude can be increased (alternatively, or additionally, the pulse width and/or pulse repetition rate can be increased). Conversely, if the frequency content of the sensed DRG signal is closer to the second frequency content information (corresponding to the output signal when the patient's level of pain perception is at an acceptable level), then the pulse amplitude can be decreased (alternatively, or additionally, the pulse width and/or pulse repetition rate can be decreased). In other embodiments, the only frequency content information stored is the frequency content information corresponding to the output signal when the patient's level of pain perception is at an acceptable level. In such embodiments, if the frequency content of a sensed output signal is not within a threshold level of the stored frequency content information, then the pulse amplitude can be increased (alternatively, or additionally, the pulse width and/or pulse repetition rate can be increased). Conversely, if the frequency content of the sensed output signal is within the threshold level of the stored frequency content information, then the pulse amplitude can be decreased to attempt to reduce power consumption (alternatively, or additionally, pulse width and/or pulse repetition rate can be decreased).

In still other embodiments, one or more of pulse amplitude, pulse width or pulse repetition rate are adjusted in a closed loop manner to cause the frequency content of a sensed output signal to be within a threshold level of the stored frequency content information corresponding to the output signal when the patient's level of pain perception is at an acceptable level.

Various embodiments of the present invention, which were described above, can be used to automatically turn on and off stimulation delivered to a target DRG by an INS and/or to automatically adjust stimulation parameters using closed loop feedback. If desired, such embodiments can be used to reduce or eliminate the need for a patient to carry around a patient programmer that enables them to adjust their stimulation. Nevertheless, a patient may still want to have the ability to override the automatic turning on and off of stimulation. Further, a patient may still want to have the ability to override the automatic adjusting of stimulation parameters (e.g., pulse amplitude). Thus, in accordance with certain embodiments, a patient programmer (e.g., 122b) can still be used to override any of the aforementioned automatic adjustments. For example, in certain embodiments, a programmer can be used to select whether an INS should operate in an automatic adjustment mode or a manual adjustment mode. Further, even when in the automatic adjustment mode, the programmer can still be used to override the automatic adjustments. For example, using embodiments of the present invention described above, an INS may turn off stimulation based on the INS's analysis of one or more sensed signals. However, a patient may decide that they would prefer to receive stimulation, and the patient can use their programmer to turn the stimulation back on. For another example, using embodiments of the present invention described above, an INS may reduce the amplitude of stimulation pulses based on the INS's analysis of one or more sensed signals. However, a patient may decide that they would prefer to increase the pulse amplitude, and the patient can use their programmer to do so. These adjustments made by the patient can also be used to modify or titrate the automatic adjustment such that the patient's desire stimulation pattern or strength is more faithfully produced by the automatic adjustments. For example, the metrics use for automatic control may be altered to be more or less aggressive based on the patient's interactions.

While the above described embodiments primarily focused on stimulation of a target DRG for the treatment of pain, embodiments of the present invention can also be used to selectively turn stimulation of a target DRG on and off, and/or adjust stimulation parameters, where stimulation of the target DRG is used for other purposes, such as treatment of itching, Parkinson's Disease, Multiple Sclerosis, movement disorders, spinal cord injury, asthma, chronic heart failure, obesity or stroke (particularly acute ischemia), to name a few.

In the embodiments described above, the electronic circuitry (e.g., 118) of the INS and the components of the programmer(s) (e.g., 122a or 122b) can be considered a data processing system of a neurostimulation system. Generally, the data processing system included in embodiments of the invention may include at least one processor (or other controller), which will typically include circuitry implanted in the patient, circuitry external of the patient, or both. When external processor circuitry is included in the data processing system, it may include one or more proprietary processor boards, and/or may make use of a general purpose desktop computer, notebook computer, handheld computer, or the like. The external processor may communicate with a number of peripheral devices (and/or other processors) via a bus subsystem, and these peripheral devices may include a data and/or programming storage subsystem or memory. The peripheral devices may also include one or more user interface input devices, user interface output devices, and a network interface subsystem to provide an interface with other processing systems and networks such as the Internet, an intranet, an Ethernet™, and/or the like. Implanted circuitry of the processor system may have some or all of the constituent components described above for external circuitry, with peripheral devices that provide user input, user output, and networking generally employing wireless communication capabilities, although hard-wired embodiments or other trans-cutaneous telemetry techniques could also be employed.

An external or implanted memory (e.g., 139 and/or 149) of the processor system can be used to store, in a tangible storage media, machine readable instructions or programming in the form of a computer executable code embodying one or more of the methods described herein. The memory may also similarly store data for implementing one or more of these methods. The memory may, for example, include a random access memory (RAM) for storage of instructions and data during program execution, and/or a read only memory (ROM) in which fixed instructions are stored. Persistent (non-volatile) storage may be provided, and/or the memory may include a hard disk drive, a compact digital read only memory (CD-ROM) drive, an optical drive, DVD, CD-R, CD-RW, solid-state removable memory, and/or other fixed or removable media cartridges or disks. Some or all of the stored programming code may be altered after implantation and/or initial use of the device to alter functionality of the stimulator system.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention.

Although the foregoing invention has been described in some detail by way of illustration and example, for purposes of clarity and understanding, it will be obvious that various alternatives, modifications and equivalents may be used and the above description should not be taken as limiting in scope of the invention.

What is claimed is:

1. A method for use by an implanted system including an implantable neurostimulator (INS) to which is connected one or more leads each having one or more electrodes,
   the method for efficiently treating targeted pain in a patient by selectively delivering electrical stimulation to a target dorsal root ganglion (DRG),
   wherein the target DRG is connected between adjacent distal sensory nerve fibers and adjacent proximal sensory nerve fibers,
      the adjacent distal sensory nerve fibers propagating an electrical signal from a periphery of the patient toward the target DRG, and
      the adjacent proximal sensory nerve fibers propagating an electrical signal away from the target DRG toward a central nervous system of the patient,
   the method comprising:
   (a) using at least one of the one or more electrodes of the one or more leads to obtain both
      (a.1) an input signal indicative of an electrical field resulting from an electrical signal propagated by the adjacent distal sensory nerve fibers toward the target DRG; and
      (a.2) an output signal indicative of an electrical field resulting from an electrical signal propagated by the adjacent proximal sensory nerve fibers away from the target DRG;
   (b) comparing the output signal to the input signal; and
   (c) selectively turning on and off delivery of the electrical stimulation to the target DRG based on results of the comparing at step (b).

2. The method of claim 1, wherein the electrical stimulation is delivered using electrical pulses that have a pulse amplitude, a pulse width and a pulse repetition rate, and further comprising:
   (d) adjusting, based on the results of the comparing at step (b), at least one of the pulse amplitude, the pulse width or the pulse repetition rate of electrical pulses that are used when delivery of electrical stimulation is turned on.

3. The method of claim 1, wherein step (b) comprises:
   (b.1) determining an input metric indicative of how many pulses occur within a specified time period of the input signal;
   (b.2) determining an output metric indicative of how many pulses occur within a specified time period of the output signal; and
   (b.3) comparing the output metric to the input metric.

4. The method of claim 1, wherein step (b) comprises:
   (b.1) determining an input metric indicative of an amplitude of pulses of the input signal;
   (b.2) determining an output metric indicative of an amplitude of pulses of the output signal; and
   (b.3) comparing the output metric to the input metric.

5. The method of claim 1, wherein step (b) comprises:
(b.1) determining an input metric indicative of a width of pulses of the input signal;
(b.2) determining an output metric indicative of a width of pulses of the output signal; and
(b.3) comparing the output metric to the input metric.

6. A method for use by an implanted system including an implantable neurostimulator (INS) to which is connected one or more leads each having one or more electrodes,
the method for efficiently treating targeted pain in a patient by selectively delivering electrical stimulation to a target dorsal root ganglion (DRG),
wherein the target DRG is connected between adjacent distal sensory nerve fibers and adjacent proximal sensory nerve fibers,
the adjacent distal sensory nerve fibers propagating an electrical signal from a periphery of the patient toward the target DRG, and
the adjacent proximal sensory nerve fibers propagating an electrical signal away from the target DRG toward a central nervous system of the patient,
the method comprising:
(a) using at least one of the one or more electrodes of the one or more leads to obtain a DRG signal indicative of an electrical field produced by cell bodies of primary sensory neurons within the target DRG and resulting from an electrical signal propagated by sensory nerve fibers within the target DRG;
(b) determining a DRG metric of the DRG signal and comparing the DRG metric to a corresponding threshold; and
(c) selectively turning on and off delivery of the electrical stimulation to the target DRG based on results of the comparing at step (b).

7. The method of claim 6, wherein step (b) comprises:
(b.1) determining a DRG metric indicative of how many pulses occur during a specified time period of the DRG signal; and
(b.2) comparing the DRG metric to a corresponding threshold.

8. The method of claim 6, wherein step (b) comprises:
(b.1) determining a DRG metric indicative of an amplitude of pulses of the DRG signal; and
(b.2) comparing the DRG metric to a corresponding threshold.

9. The method of claim 6, wherein step (b) comprises:
(b.1) determining a DRG metric indicative of a width of pulses of the DRG signal; and
(b.2) comparing the DRG metric to a corresponding threshold.

10. The method of claim 6, further comprising:
(d) adjusting, based on the results of the comparing at step (b), at least one of pulse amplitude, pulse width or pulse repetition rate of electrical pulses that are used for delivering electrical stimulation to the target DRG.

11. A method for use by an implanted system including an implantable neurostimulator (INS) to which is connected one or more leads each having one or more electrodes,
the method for efficiently treating targeted pain in a patient by selectively delivering electrical stimulation to a target dorsal root ganglion (DRG),
wherein the target DRG is connected between adjacent distal sensory nerve fibers and adjacent proximal sensory nerve fibers,
the adjacent distal sensory nerve fibers propagating an electrical signal from a periphery of the patient toward the target DRG, and
the adjacent proximal sensory nerve fibers propagating an electrical signal away from the target DRG toward a central nervous system of the patient,
the method comprising:
(a) using at least one of the one or more electrodes of the one or more leads to obtain a DRG signal indicative of an electrical field produced by cell bodies of primary sensory neurons within the target DRG and resulting from an electrical signal propagated by sensory nerve fibers within the target DRG;
(b) at least one of
comparing morphology of the DRG signal to one or more stored morphological templates; or
comparing frequency content of the DRG signal to stored information indicative of frequency content; and
(c) selectively turning on and off delivery of the electrical stimulation to the target DRG based on results of the comparing at step (b).

12. The method of claim 11, wherein:
step (b) comprises comparing frequency content of the DRG signal to stored information indicative of frequency content.

13. The method of claim 11, wherein:
step (b) comprises comparing morphology of the DRG signal to one or more stored morphological templates.

14. The method of claim 11, further comprising:
(d) adjusting, based on the results of the comparing at step (b), at least one of pulse amplitude, pulse width or pulse repetition rate of electrical pulses that are used for delivering electrical stimulation to the target DRG.

15. A method for use by an implanted system including an implantable neurostimulator (INS) to which is connected one or more leads each having one or more electrodes,
the method for efficiently treating targeted pain in a patient by selectively delivering electrical stimulation to a target dorsal root ganglion (DRG),
wherein the target DRG is connected between adjacent distal sensory nerve fibers and adjacent proximal sensory nerve fibers,
the adjacent distal sensory nerve fibers propagating an electrical signal from a periphery of the patient toward the target DRG, and
the adjacent proximal sensory nerve fibers propagating an electrical signal away from the target DRG toward a central nervous system of the patient,
the method comprising:
(a) using at least one of the one or more electrodes of the one or more leads to obtain an output signal indicative of an electrical field resulting from an electrical signal propagated by the adjacent proximal sensory nerve fibers away from the target DRG;
(b) determining an output metric of the output signal and comparing the output metric to a corresponding threshold; and
(c) selectively turning on and off delivery of the electrical stimulation to the target DRG based on results of the comparing at step (b).

16. The method of claim 15, wherein step (b) comprises:
(b.1) determining an output metric indicative of how many pulses occur within a specified time period of the output signal; and
(b.2) comparing the output metric to a corresponding threshold.

17. The method of claim 15, wherein step (b) comprises:
(b.1) determining an output metric indicative of an amplitude of pulses of the output signal; and (b.2) comparing the output metric to a corresponding threshold.

18. The method of claim 15, wherein step (b) comprises:
(b.1) determining an output metric indicative of a width of pulses of the output signal; and
(b.2) comparing the output metric to a corresponding threshold.

19. The method of claim 15, further comprising:
(d) adjusting, based on the results of the comparing at step (b), at least one of pulse amplitude, pulse width or pulse repetition rate of electrical pulses that are used for delivering electrical stimulation to the target DRG.

20. A method for use by an implanted system including an implantable neurostimulator (INS) to which is connected one or more leads each having one or more electrodes,
the method for efficiently treating targeted pain in a patient by selectively delivering electrical stimulation to a target dorsal root ganglion (DRG),
wherein the target DRG is connected between adjacent distal sensory nerve fibers and adjacent proximal sensory nerve fibers,
the adjacent distal sensory nerve fibers propagating an electrical signal from a periphery of the patient toward the target DRG, and
the adjacent proximal sensory nerve fibers propagating an electrical signal away from the target DRG toward a central nervous system of the patient,
the method comprising:
(a) using at least one of the one or more electrodes of the one or more leads to obtain an output signal indicative of an electrical field resulting from an electrical signal propagated by the adjacent proximal sensory nerve fibers away from the target DRG;
(b) at least one of
comparing morphology of the output signal to one or more stored morphological templates; or
comparing frequency content of the output signal to stored information indicative of frequency content; and
step (c) comprises selectively turning on and off delivery of the electrical stimulation to the target DRG based on results of the comparing at step (b).

21. The method of claim 20, wherein:
step (b) comprises comparing frequency content of the output signal to stored information indicative of frequency content.

22. The method of claim 20, further comprising:
(d) adjusting, based on the results of the comparing at step (b), at least one of pulse amplitude, pulse width or pulse repetition rate of electrical pulses that are used for delivering electrical stimulation to the target DRG.

23. The method of claim 20, wherein:
step (b) comprises comparing morphology of the output signal to one or more stored morphological templates.

24. A method for use by an implanted system including an implantable neurostimulator (INS) to which is connected one or more leads each having one or more electrodes,
the method for efficiently treating targeted pain in a patient by selectively delivering electrical stimulation to a target dorsal root ganglion (DRG),
wherein the target DRG is connected between adjacent distal sensory nerve fibers and adjacent proximal sensory nerve fibers,
the adjacent distal sensory nerve fibers propagating an electrical signal from a periphery of the patient toward the target DRG, and
the adjacent proximal sensory nerve fibers propagating an electrical signal away from the target DRG toward a central nervous system of the patient,
the method comprising:
(a) using at least one of the one or more electrodes of the one or more leads to obtain both
(a.1) an input signal indicative of an electrical field resulting from an electrical signal propagated by the adjacent distal sensory nerve fibers toward the target DRG; and
(a.2) an output signal indicative of an electrical field resulting from an electrical signal propagated by the adjacent proximal sensory nerve fibers away from the target DRG;
(b) comparing the output signal to the input signal; and
(c) adjusting, based on the results of the comparing at step (b), at least one of pulse amplitude, pulse width or pulse repetition rate of electrical pulses that are used for delivering electrical stimulation to the target DRG.

25. A method for use by an implanted system including an implantable neurostimulator (INS) to which is connected one or more leads each having one or more electrodes,
the method for efficiently treating targeted pain in a patient by selectively delivering electrical stimulation to a target dorsal root ganglion (DRG),
wherein the target DRG is connected between adjacent distal sensory nerve fibers and adjacent proximal sensory nerve fibers,
the adjacent distal sensory nerve fibers propagating an electrical signal from a periphery of the patient toward the target DRG, and
the adjacent proximal sensory nerve fibers propagating an electrical signal away from the target DRG toward a central nervous system of the patient,
the method comprising:
(a) using at least one of the one or more electrodes of the one or more leads to obtain a DRG signal indicative of an electrical field produced by cell bodies of primary sensory neurons within the target DRG and resulting from an electrical signal propagated by sensory nerve fibers within the target DRG;
(b) at least one of
determining a DRG metric of the DRG signal and comparing the DRG metric to a corresponding threshold;
comparing morphology of the DRG signal to one or more stored morphological templates; or
comparing frequency content of the DRG signal to stored information indicative of frequency content; and
(c) adjusting, based on the results of the comparing at step (b), at least one of the pulse amplitude, the pulse width or the pulse repetition rate of the electrical pulses that are used for delivering electrical stimulation to the target DRG.

26. The method of claim 25 wherein:
step (b) comprises comparing morphology of the DRG signal to one or more stored morphological templates.

27. The method of claim 25, wherein:
step (b) comprises comparing frequency content of the DRG signal to stored information indicative of frequency content.

28. The method of claim 25, wherein:
step (b) comprises determining a DRG metric of the DRG signal and comparing the DRG metric to a corresponding threshold.

29. A method for use by an implanted system including an implantable neurostimulator (INS) to which is connected one or more leads each having one or more electrodes, the method for efficiently treating targeted pain in a patient by selectively delivering electrical stimulation to a target dorsal root ganglion (DRG), wherein the target DRG is connected between adjacent distal sensory nerve fibers and adjacent proximal sensory nerve fibers, the adjacent distal sensory nerve fibers propagating an electrical signal from a periphery of the patient toward the target DRG, and the adjacent proximal sensory nerve fibers propagating an electrical signal away from the target DRG toward a central nervous system of the patient, the method comprising:

(a) using at least one of the one or more electrodes of the one or more leads to obtain an output signal indicative of an electrical field resulting from an electrical signal propagated by the adjacent proximal sensory nerve fibers away from the target DRG;

(b) at least one of determining an output metric of the output signal and comparing the output metric to a corresponding threshold;

comparing morphology of the output signal to one or more stored morphological templates; or comparing frequency content of the output signal to stored information indicative of frequency content; and (c) adjusting, based on the results of the comparing at step (b), at least one of the pulse amplitude, the pulse width or the pulse repetition rate of the electrical pulses that are used for delivering electrical stimulation to the target DRG.

30. The method of claim 29, wherein:

step (b) comprises comparing morphology of the output signal to one or more stored morphological templates.

31. The method of claim 29, wherein:

step (b) comprises comparing frequency content of the output signal to stored information indicative of frequency content.

32. The method of claim 29, wherein:

step (b) comprises determining an output metric of the output signal and comparing the output metric to a corresponding threshold.

33. An implantable system for efficiently treating targeted pain in a patient by selectively delivering electrical stimulation to a target dorsal root ganglion (DRG), wherein the target DRG is connected between adjacent distal sensory nerve fibers and adjacent proximal sensory nerve fibers, the adjacent distal sensory nerve fibers propagating an electrical signal from a periphery of the patient toward the target DRG, and the adjacent proximal sensory nerve fibers propagating an electrical signal away from the target DRG toward a central nervous system of the patient, the system comprising:

one or more implantable leads each having one or more electrodes;

a pulse generator configured to generate electrical stimulation pulses that can be delivered to the target DRG via one or more electrodes of the one or more leads;

sensing circuitry configured to use at least one of the one or more electrodes of the one or more leads to obtain both an input signal indicative of an electrical field resulting from an electrical signal propagated by the adjacent distal sensory nerve fibers toward the target DRG; and an output signal indicative of an electrical field resulting from an electrical signal propagated by the adjacent proximal sensory nerve fibers away from the target DRG;

a controller configured to compare the output signal to the input signal, and in response thereto, at least one of selectively turn on and off delivery of the electrical stimulation to the target DRG; or adjust at least one of a pulse amplitude, a pulse width or a pulse repetition rate of electrical pulses that are used for delivering electrical stimulation to the target DRG.

34. An implantable system for efficiently treating targeted pain in a patient by selectively delivering electrical stimulation to a target dorsal root ganglion (DRG), wherein the target DRG is connected between adjacent distal sensory nerve fibers and adjacent proximal sensory nerve fibers, the adjacent distal sensory nerve fibers propagating an electrical signal from a periphery of the patient toward the target DRG, and the adjacent proximal sensory nerve fibers propagating an electrical signal away from the target DRG toward a central nervous system of the patient, the system comprising:

one or more implantable leads each having one or more electrodes;

a pulse generator configured to generate electrical stimulation pulses that can be delivered to the target DRG via one or more electrodes of the one or more leads;

sensing circuitry configured to use at least one of the one or more electrodes of the one or more leads to obtain a DRG signal indicative of an electrical field produced by cell bodies of primary sensory neurons within the target DRG and resulting from an electrical signal propagated by sensory nerve fibers within the target DRG;

a controller configured to at least one of determine a DRG metric of the DRG signal and compare the DRG metric to a corresponding threshold;

compare morphology of the DRG signal to one or more stored morphological templates; or compare frequency content of the DRG signal to stored information indicative of frequency content; and in response thereto, at least one of selectively turn on and off delivery of the electrical stimulation to the target DRG; or adjust at least one of a pulse amplitude, a pulse width or a pulse repetition rate of electrical pulses that are used for delivering electrical stimulation to the target DRG.

35. An implantable system for efficiently treating targeted pain in a patient by selectively delivering electrical stimulation to a target dorsal root ganglion (DRG), wherein the target DRG is connected between adjacent distal sensory nerve fibers and adjacent proximal sensory nerve fibers, the adjacent distal sensory nerve fibers propagating an electrical signal from a periphery of the patient toward the target DRG, and the adjacent proximal sensory nerve fibers propagating an electrical signal away from the target DRG toward a central nervous system of the patient, the system comprising:

one or more implantable leads each having one or more electrodes;

a pulse generator configured to generate electrical stimulation pulses that can be delivered to the target DRG via one or more electrodes of the one or more leads;

sensing circuitry configured to use at least one of the one or more electrodes of the one or more leads to obtain an output signal indicative of an electrical field resulting from an electrical signal propagated by the adjacent proximal sensory nerve fibers away from the target DRG;

a controller configured to at least one of determine an output metric of the output signal and compare the output metric to a corresponding threshold;

compare morphology of the output signal to one or more stored morphological templates; or compare frequency content of the output signal to stored information indicative of frequency content;

and in response thereto, at least one of selectively turn on and off delivery of the electrical stimulation to the target DRG; or adjust at least one of a pulse amplitude, a pulse width or a pulse repetition rate of electrical pulses that are used for delivering electrical stimulation to the target DRG.

\* \* \* \* \*